(12) United States Patent
Gross et al.

(10) Patent No.: US 8,196,470 B2
(45) Date of Patent: Jun. 12, 2012

(54) WIRELESS INTERFACE FOR AUDIOMETERS

(75) Inventors: Allan H. Gross, Carmel, IN (US);
Barak Dar, Minnetonka, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 249 days.

(21) Appl. No.: 11/679,959

(22) Filed: Feb. 28, 2007

(65) Prior Publication Data

US 2007/0204695 A1    Sep. 6, 2007

Related U.S. Application Data

(60) Provisional application No. 60/777,778, filed on Mar. 1, 2006.

(51) Int. Cl.
*G01N 29/30* (2006.01)
*A61B 5/12* (2006.01)

(52) U.S. Cl. .............................. 73/585; 600/559; 381/60

(58) Field of Classification Search ................ 73/585; 600/558–559; 381/60
See application file for complete search history.

(56) References Cited

U.S. PATENT DOCUMENTS

| | | | | |
|---|---|---|---|---|
| 4,187,413 A * | 2/1980 | Moser | | 381/320 |
| 4,964,304 A * | 10/1990 | Eckstein | | 73/585 |
| 5,197,332 A * | 3/1993 | Shennib | | 73/585 |
| 5,710,819 A * | 1/1998 | Topholm et al. | | 381/316 |
| 6,035,050 A * | 3/2000 | Weinfurtner et al. | | 381/313 |
| 6,115,478 A * | 9/2000 | Schneider | | 381/314 |
| 6,532,296 B1 | 3/2003 | Vaudrey | | |
| 6,644,120 B1 * | 11/2003 | Braun et al. | | 73/585 |
| 6,648,820 B1 * | 11/2003 | Sarel | | 600/300 |
| 6,840,908 B2 * | 1/2005 | Edwards et al. | | 600/559 |
| 6,895,345 B2 * | 5/2005 | Bye et al. | | 702/57 |
| 7,018,342 B2 * | 3/2006 | Harrison et al. | | 600/559 |
| 7,190,795 B2 * | 3/2007 | Simon | | 381/60 |
| 7,616,771 B2 * | 11/2009 | Lenhardt et al. | | 381/326 |
| 2002/0026125 A1 * | 2/2002 | Leysieffer | | 600/559 |
| 2002/0048374 A1 * | 4/2002 | Soli et al. | | 381/60 |
| 2002/0165466 A1 * | 11/2002 | Givens et al. | | 600/559 |
| 2003/0065276 A1 | 4/2003 | Akita | | |
| 2004/0037428 A1 * | 2/2004 | Keller | | 381/60 |
| 2004/0049125 A1 | 3/2004 | Nakamura | | |
| 2004/0165731 A1 * | 8/2004 | Ribic | | 381/60 |
| 2004/0204921 A1 * | 10/2004 | Bye et al. | | 702/189 |
| 2004/0254753 A1 | 12/2004 | Bengtsson | | |
| 2005/0129262 A1 * | 6/2005 | Dillon et al. | | 381/312 |
| 2007/0133832 A1 * | 6/2007 | DiGiovanni et al. | | 381/320 |
| 2007/0147641 A1 * | 6/2007 | Platz | | 381/315 |
| 2008/0008328 A1 * | 1/2008 | Hansson | | 381/58 |
| 2008/0056518 A1 * | 3/2008 | Burrows et al. | | 381/314 |
| 2008/0167575 A1 * | 7/2008 | Cronin et al. | | 600/559 |

FOREIGN PATENT DOCUMENTS

| | | |
|---|---|---|
| WO | 01/22777 | 3/2001 |
| WO | 02/089520 | 11/2002 |
| WO | 2004/004414 | 1/2004 |

OTHER PUBLICATIONS

International Search Report; PCT/US2007/005373; Oct. 29, 2007.

* cited by examiner

*Primary Examiner* — Helen C. Kwok

(57) ABSTRACT

An interface adapted for use with an audiometer, including a digital wireless interface supported by a base unit and a remote unit wherein the base unit receives signals from the audiometer and provides the signals to the remote unit via the digital wireless interface.

30 Claims, 20 Drawing Sheets

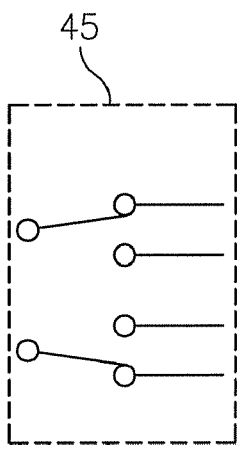 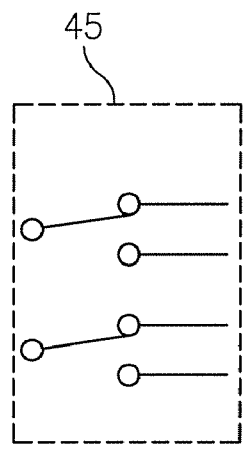 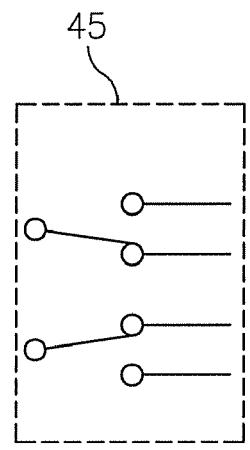
*FIG. 3E*   *FIG. 3F*   *FIG. 3G*
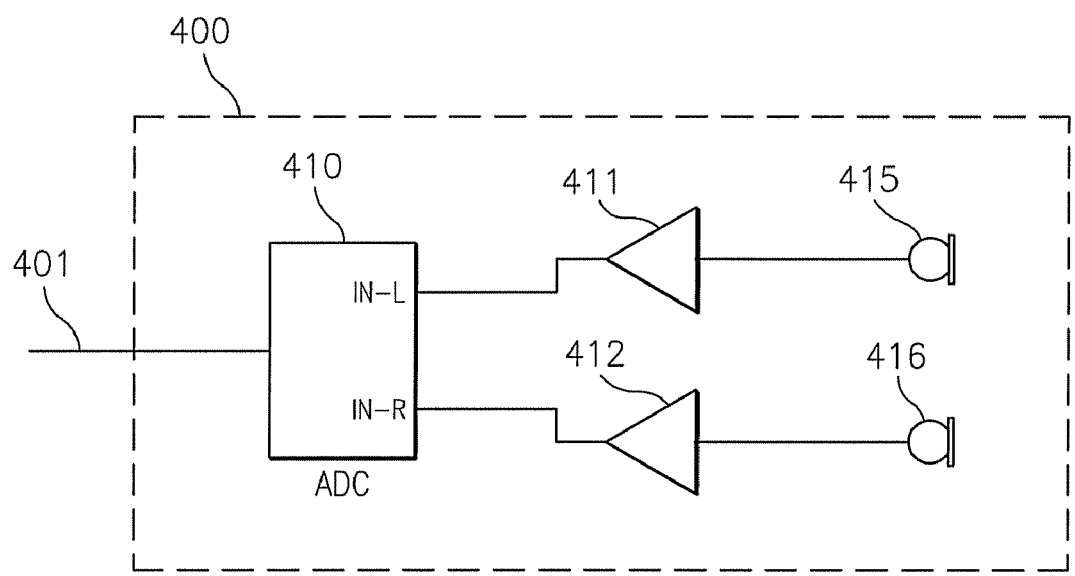
*FIG. 3H*

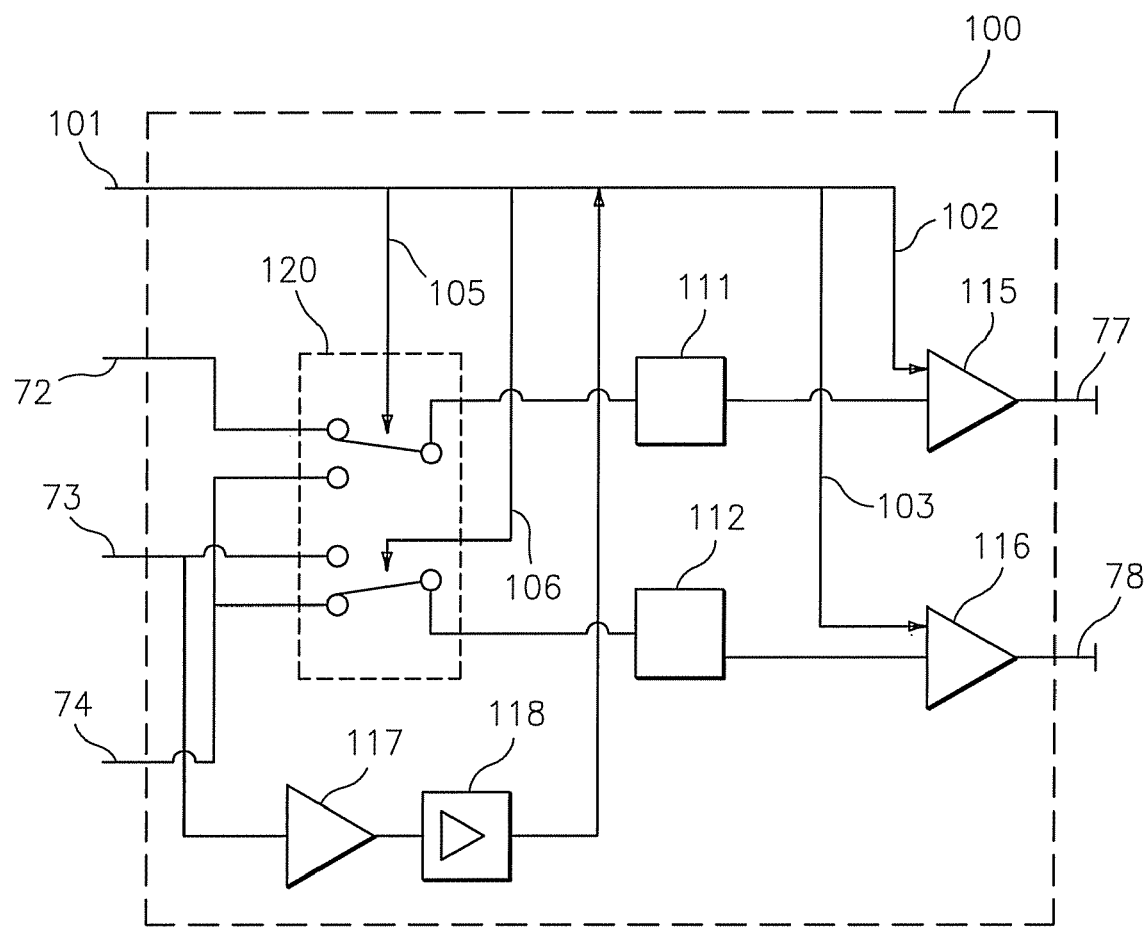
*FIG. 4B*
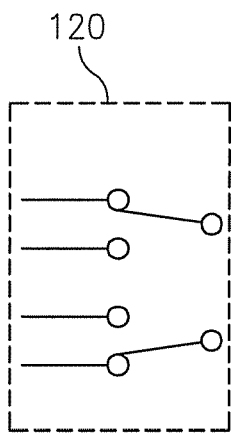 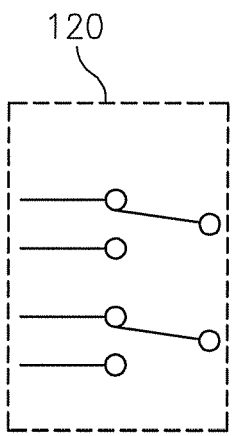 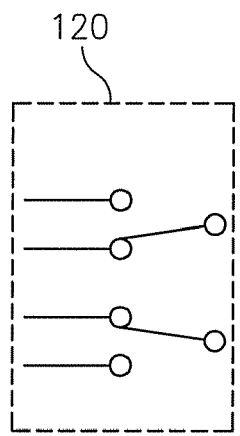
*FIG. 4C*   *FIG. 4D*   *FIG. 4E*

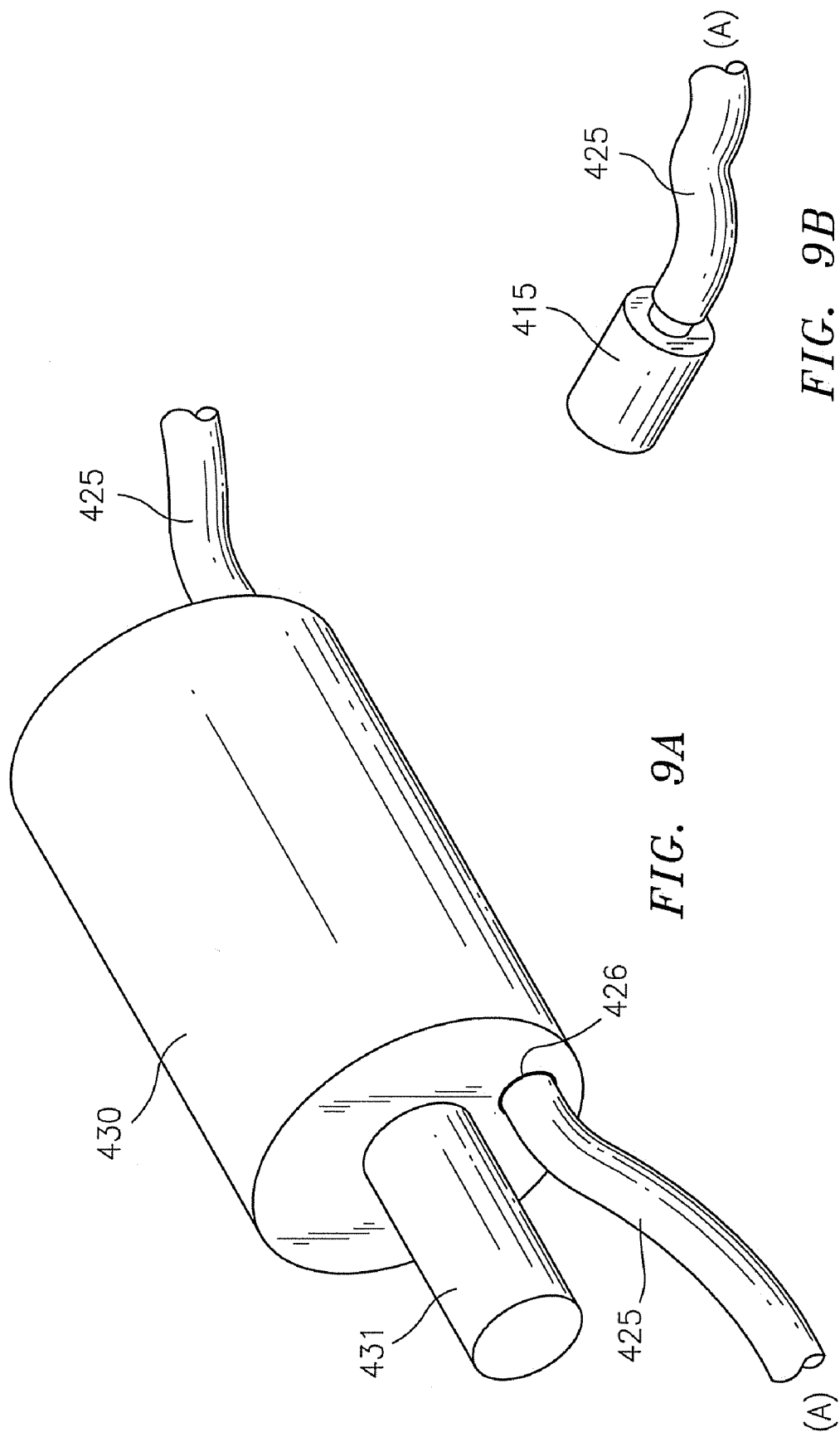

WIRELESS INTERFACE FOR AUDIOMETERS

CROSS-REFERENCES TO RELATED APPLICATIONS

This application is filed under 37 CFR 1.53(b) and claims the benefit of U.S. Provisional Application No. 60/777,778, filed Mar. 1, 2006, "WIRELESS INTERFACE FOR AUDIOMETERS," the entire disclosure of which is incorporated by reference herein in its entirety.

BACKGROUND OF THE INVENTION

1. Field of the Invention

The present invention relates to the field of audiometric testing.

2. Description of the Related Art

Audiometer systems are used to test hearing of people referred to as test subjects. In general, an audiometer provides electrical signals to earphones. The earphones are placed one of over and in the ears of the test subject. The earphones convert the electrical signals to audible test sounds at the ears of the test subject. The test subject typically raises a hand or finger in response to detecting a test sound.

Prior art audiometer systems use wire tethers to connect the audiometer to the earphones. A bone conduction transducer may be used in addition to the earphones. In the art, the bone conduction transducer may also be referred to as an oscillator or a vibrator. The audiometer system may also have a user response button as an indicator to the examiner of the test subject's detection of the test sounds. Where recorded or live speech is used as test material, a response from the test subject will generally be verbal. The response will typically be communicated to the examiner via a microphone positioned inside an audiometric test booth.

The wire tethers are a weak and bothersome link. Approximately 80% of audiometer system failures result from failures of the wire tethers. When the wire tethers fail, costs accrue from repair bills and downtime. The wire tethers add to space requirements in portable audiometer systems. Additionally, the wire tethers add to the time and inconvenience associated with setting up and dismantling the portable audiometer systems. The wire tethers confine the test subject to a chair within the audiometric test booth. Confinement to the chair may severely limit testing with young children who may have limited or no tolerance for that restriction.

Design improvements to wire tethered systems have included evaluation of wireless links. Audiometer systems with the wireless link must provide the same sound signals with the same accuracy as the audiometer systems with the wire tether. For example, the audiometer systems must produce signals in a very wide dynamic range. A clinical audiometer must produce sounds in the range −10 dBHL to 110 dBHL (wherein HL refers to Hearing Level). Audiometers must comply with US and international standards including ANSI S3.6-2004, "Specification for Audiometers" and ISO 389-2 "Acoustics—Reference zero for the calibration of audiometric equipment—Part 2: Reference equivalent threshold sound pressure levels for pure tones and insert earphone." Test environments must comply with ANSI S3.1-1999 "Maximum Permissible Ambient Noise Levels for Audiometric Test Rooms." These standards include requirements for high signal to noise ratio, low harmonic distortion, and high adjacent channel rejection.

Early attempts at using the wireless link were based on analog FM radio technology. However, the analog FM radio technology cannot transmit the wide dynamic range required from the clinical audiometer. A high quality FM transmitter cannot transmit a linear signal with more than approximately 70 dB of dynamic range. It is also known that in order to transmit a wider dynamic range, the analog FM transmitter must incorporate an analog COMPANDER (non-linear audio processing that compresses a signal at the input to a transmitter and expands the signal at the output from a receiver). In the field of audiometric testing it is unacceptable to apply non-linear processing to the electrical signals transmitted (also referred to as test signals) to the earphones. Furthermore, accurate audiometric testing requires very stable conditions without interferences and fluctuations of the test signals. Analog FM radio systems are susceptible to radio signal interferences. Additionally, noise levels of the analog FM radio signals are subject to reception conditions. Another known problem of the analog FM transmitters is poor channel rejection in cases when two or more channels (i.e., stereo) are multiplexed on a same radio carrier signal.

U.S. Pat. No. 4,964,304, dated Oct. 23, 1990, entitled "AUDIOMETRIC TESTING METHOD AND APPARATUS," discloses "Means for transmitting an FM radio signal carrying an audio test signal to a preselected one of two receivers in the headset of a patient, together with FM signalling means carried by the patient to transmit signals to the audiometer indicating which of the patient's ears received the test signal to permit the patient to have virtually unlimited mobility during the testing procedure. Separate FM signal channels may be provided to permit simultaneous testing of a plurality of patients. Furthermore, if desired, a predetermined pattern of test signals may be recorded and means may be provided for automatically transmitting the test signals and recording the patient response signals, thereby permitting fully automatic testing to be conducted."

What are needed are methods and apparatus for providing more reliable and convenient electrical signal connections in audiometer systems.

BRIEF SUMMARY OF THE INVENTION

The shortcomings of the prior art are overcome and additional advantages are provided through an interface adapted for use with an audiometer, the interface includes a digital wireless interface supported by a base unit and a remote unit wherein the base unit receives signals from the audiometer and provides the signals to the remote unit via the digital wireless interface.

Also disclosed is a base unit adapted for receiving signals from an audiometer including a receiver for receiving test sound information and transmitting encoded test sound information to a remote unit through a digital wireless interface.

Also disclosed is a remote unit adapted for providing a test sound, the remote unit includes a digital wireless interface for receiving encoded test sound information and outputting a test sound signal to a transducer for providing the test sound.

Also disclosed is a method for conducting an audiometric test of a test subject, the method includes receiving test sound information; and using a digital wireless interface, providing the test sound information to the test subject as at least one test sound.

Also disclosed is a system for conducting audiometric tests, the system includes means for receiving test sound information; means for producing encoded test sound information; means for transmitting the encoded test sound information over a digital wireless interface; means for receiving the encoded test sound information; and means for producing test sounds.

Also disclosed is an audiometer adapted for providing input to a remote unit, including a test sound information generator for generating test sounds and a transceiver for transmitting encoded test sound information to the remote unit through a digital wireless interface.

Further disclosed is a method for calibrating an audiometric testing system having a digital wireless interface, the method includes producing a test sound in an ear canal of a test subject; monitoring a corresponding sound pressure level; and adjusting the audiometric testing system to match the sound pressure level to a predetermined value.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE DRAWINGS

FIG. 3E illustrates an exemplary schematic diagram of a first position of a de-multiplexer;

FIG. 3F illustrates an exemplary schematic diagram of a second position of the de-multiplexer;

FIG. 3G illustrates an exemplary schematic diagram of a third position of the de-multiplexer;

FIG. 3H illustrates an exemplary schematic diagram of a calibration block;

FIG. 4B illustrates an exemplary schematic diagram of a signal conditioning and multiplexing block;

FIG. 4C illustrates an exemplary schematic diagram a first position of a multiplexer;

FIG. 4D illustrates an exemplary schematic diagram of a second position of the multiplexer;

FIG. 4E illustrates an exemplary schematic diagram of a third position of the multiplexer;

FIG. 9A illustrates an exemplary embodiment of an insert earphone tip;

FIG. 9B illustrates an exemplary embodiment of a sensing tube connected to a miniature microphone;

DETAILED DESCRIPTION OF THE INVENTION

The teachings provide for a digital wireless interface. The digital wireless interface provides for communicating to earphones information derived from test signals provided by an audiometer. The test signals are related to test sounds to be played to the test subject. The wireless interface may also provide for the test subject communicating back to an examiner. For example, the test subject may press a button in response to hearing a test sound. Communications from the test subject to the examiner follow the same industry protocols used for communicating the information from the audiometer to the earphones (also referred to as transducers). The wireless interface provides for meeting industry standards for audiometric testing.

Figure 1:
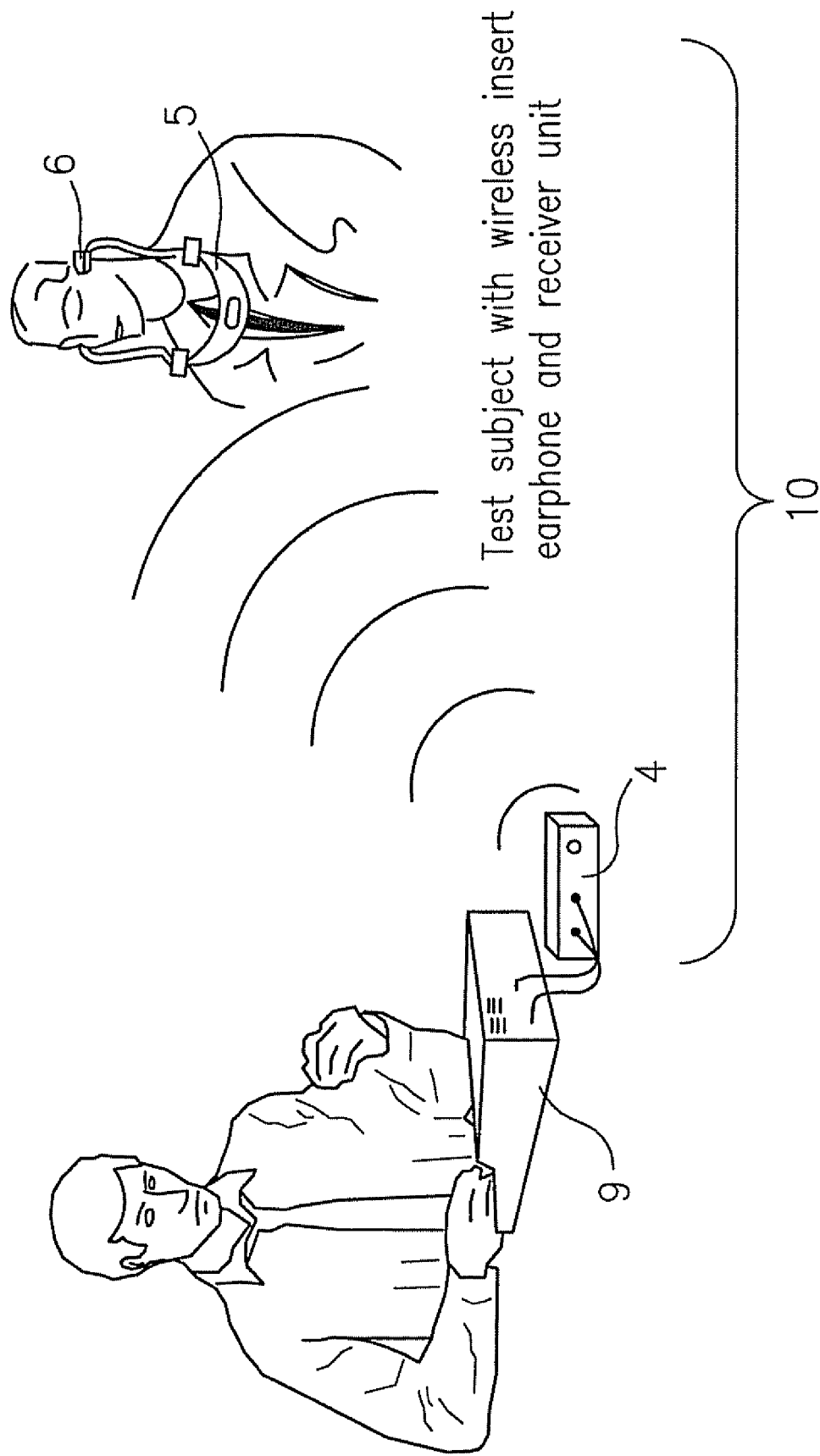
FIG. 1 illustrates an exemplary embodiment of a digital wireless interface.

FIG. 1 illustrates an exemplary embodiment a digital wireless interface 10. The digital wireless interface 10 includes a base unit 4 and a remote unit 5. An audiometer 9 provides electrical signals (test signals) corresponding to the test sounds to be presented to the test subject. The examiner operates the audiometer 9. The output from the audiometer 9 is provided as input to the base unit 4. The input is communicated to the remote unit 5. The remote unit 5 provides electrical signals to earphones 6. The earphones 6 convert the electrical signals to the test sounds. The test subject may actuate a response switch in the remote unit 5 upon recognizing the test sounds. The remote unit 5 communicates actuation of the response switch to the base unit 4. In one embodiment, the base unit 5 includes a user interface for communicating actuation of the response switch to the examiner. In general, the remote unit 5 is located in the vicinity of the earphones 6. Typically, the remote unit 5 may be one of fastened to, held by, and worn by the test subject.

The audiometer 9 may be one of an analog audiometer that provides analog output and a digital audiometer that provides digital output. The base unit 4 may include an analog input stage for receiving the analog output from the analog audiometer. The base unit 4 may also include a digital interface for receiving the digital output from the digital audiometer.

The base unit 4 and the remote unit 5 provide for two-way digital communications. Typically, the two-way communications are provided by a high density coding method including digital baseband modulation which is further modulated to create a radio frequency (RF) signal that can be sent through free space. In general, the two-way communications are conducted over a single frequency by employing two-way package based digital radio, constantly switching between transmit-receive-transmit-receive and so on. Frequency-hopping schemes may automatically change the frequency when interference is encountered. One embodiment of the high density coding method is "minimum shift keying" (MSK).

Figure 2:
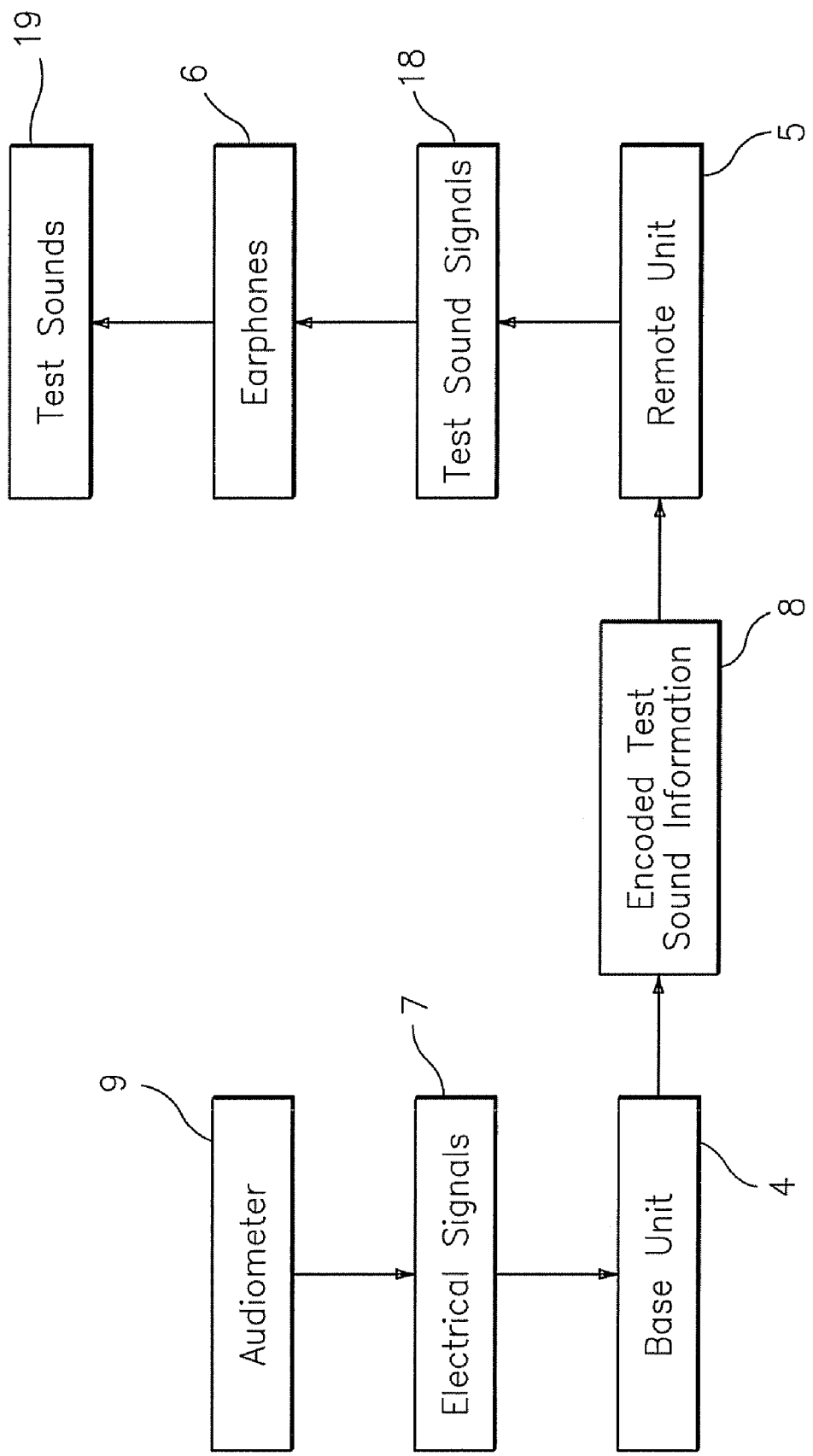
FIG. 2 illustrates an exemplary flow chart depicting operation of the digital wireless interface.

FIG. 2 illustrates an exemplary flow chart depicting operation of the digital wireless interface 10. The examiner operates the audiometer 9. The audiometer 9 provides electrical signals 7, corresponding to the test sounds, to the base unit 4. The electrical signals 7 are derived from the test sounds that the examiner intends to present to the test subject. Information transmitted from the audiometer 9 to the base unit 4 may also be referred to as test sound information. The base unit 4 encodes the electrical signals 7 to encoded test sound information 8. The encoded test sound information 8 is transmitted by the radio frequency signal to the remote unit 5. The remote unit 5 converts the encoded test sound information 8 to test sound signals 18. The test sound signals 18 are provided to the earphones 6. The earphones 6 transform the test sound signals 18 to test sounds 19 intended by the examiner for the test subject.

Figure 3A:
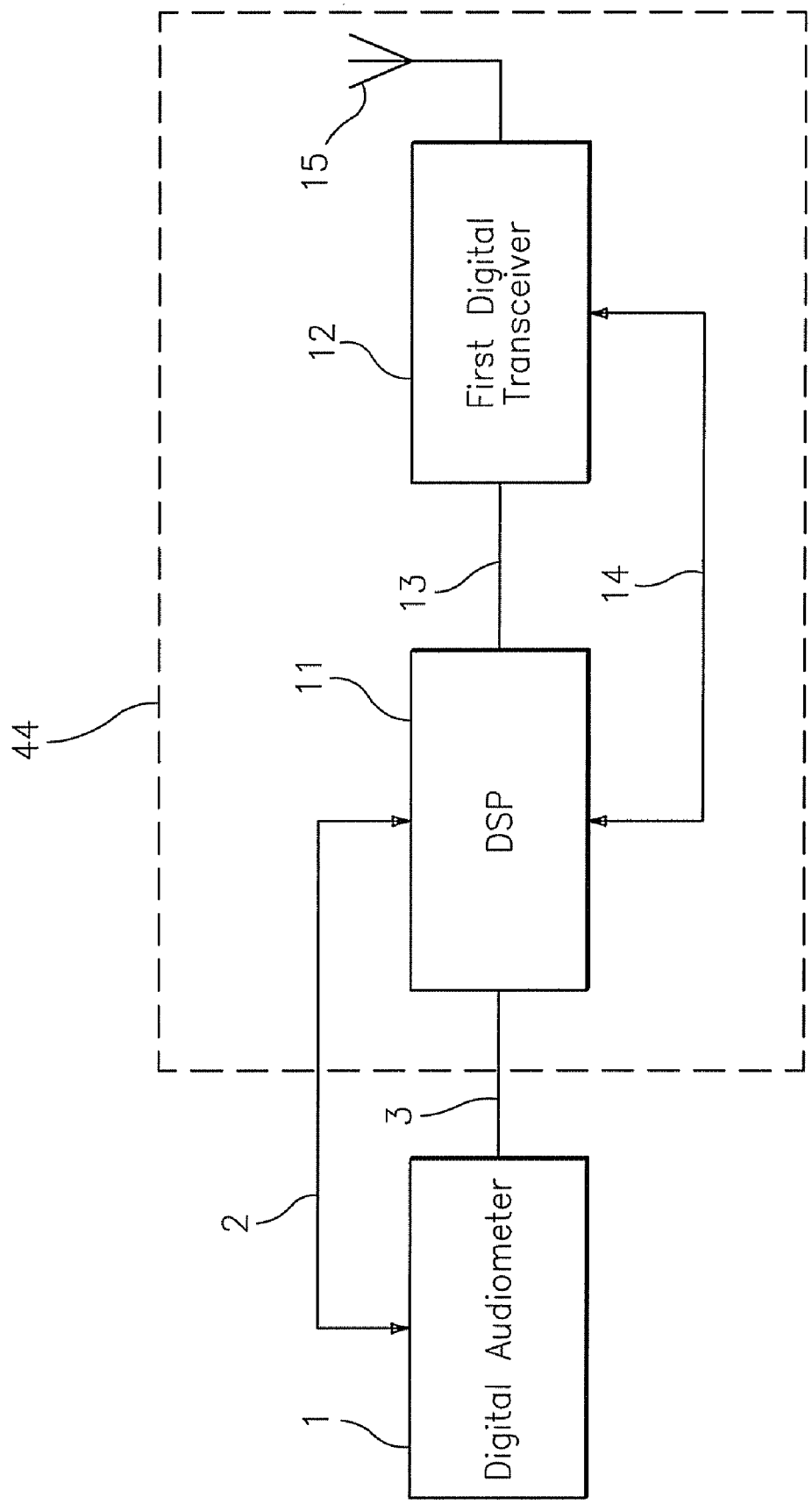
FIG. 3A illustrates an exemplary schematic diagram of a base unit connected to an audiometer with a digital output.

The base unit 4 may be connected to the digital audiometer. FIG. 3A illustrates an exemplary schematic diagram of a digital base unit 44 connected to a digital audiometer 1. In one embodiment, the digital audiometer 1 includes a computer-processing unit running a "software audiometer." The software audiometer includes software that provides for the computer-processing unit to function as the digital audiometer 1.

Referring to FIG. 3A, the digital audiometer 1 is connected to a digital signal processor (DSP) 11 via a first serial digital interface 3. Exemplary embodiments of the first serial digital interface 3 include industry standards such as Integrated Interchip Sound (I2S), Universal Serial Bus (USB), and Sony/Philips Digital Interface Format (SPDIF). Digital audio for the digital wireless interface 10 includes at least 20 bit words of uncompressed stereo digital audio format to provide 120 dB dynamic range bandwidth. A stereo capability may be included because audiometric testing may require two simultaneous channels. A minimum sampling rate of 16 kHz may be used with the DSP 11 for audiometric test frequencies of 0-8 KHz. The DSP 11 converts digital audio signals from the audiometer 1 to a serial data format suitable for digital wireless communications via a second serial digital interface 13. An exemplary embodiment of the second serial digital interface 13 is I2S with serial data, word select, and serial clock lines. A first digital transceiver 12 receives data from the second serial digital interface 13. Exemplary embodiments of the first digital transceiver 12 include Philips TEA 7000 or Nordic Semiconductor NRF24Z1 digital audio transceivers or standard wireless networking such as Bluetooth and IEEE 802.11 compliant devices. The first digital transceiver 12 typically provides for high data rates by using a high density modulating method. The high density modulating method typically includes the MSK. A digital radio signal is typically transmitted via a first antenna 15.

Typically, audio compression is not used for audiometric test applications because audio compression adds noise and does not exactly reproduce an original signal.

Since the minimum net (not including overhead to manage communications protocol) audio data rate must be at least 640 kbps (16 KHz*20 bit*2=640,000 bit per second), the first digital transceiver 12 operates at a data rate greater than 2 Mbps to handle the communications protocol, two-way communications, error corrections, etc.

Figure 3B:
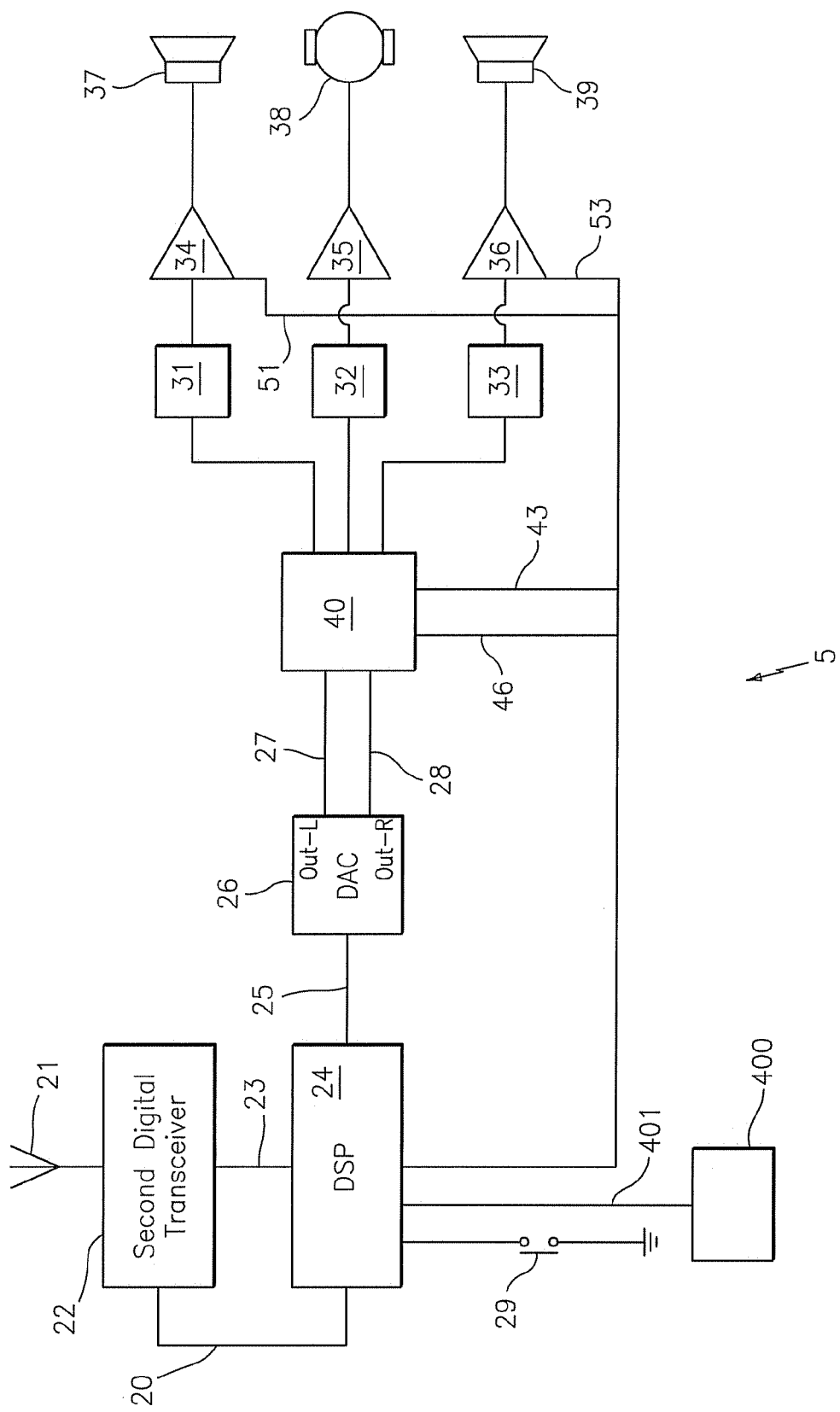
FIG. 3B illustrates an exemplary schematic diagram of a remote unit.

FIG. 3B illustrates an exemplary schematic diagram of the remote unit 5. Referring to FIG. 3B, a second digital transceiver 22 receives the digital radio signal via a second antenna 21. The second digital transceiver 22 converts and decodes the digital radio signal into a serial digital data stream 23. The serial digital data stream 23 is transmitted to a DSP 24. The DSP 24 converts the serial digital data stream 23 to a digital audio data stream 25. Typically, the digital audio data stream 25 makes use of a standard format, such as I2S for example. The digital audio data stream 25 is transmitted to a high resolution stereo digital to analog converter (DAC) 26. An exemplary embodiment of the DAC 26 is a Cirrus Logic CS4398. The DAC 26 may produce two channels of analog audio signals, a left audio output signal 27 and a right audio output signal 28. The left audio output signal 27 and the right audio output signal 28 are transmitted to a buffer and control block 40. The buffer and control block 40 produces three analog audio signals corresponding with standard audiometer signals for left phone, right phone and bone conduction. Each of the three analog audio signals is transmitted to separate band pass filters 31, 32 and 33. To preserve maximum dynamic range, digital audio is transmitted with a flat frequency response in a bandwidth corresponding with audiometric test frequencies. The band pass filters 31, 32, and 33 shape the frequency response of the analog audio signals. The frequency response is shaped in order to normalize an acoustic response of the transducers to Hearing Levels (HL) according to the "reference equivalent sound pressure level" (RETSPL) and the acoustic frequency response of the transducer. A normalized signal from each of the band pass filters 31, 32, and 33 is transmitted to separate audio amplifiers 34, 35, and 36 respectively. Output of the audio amplifier 34 is transmitted to a left earphone 37. Output of the audio amplifier 36 is transmitted to a right earphone 39. Exemplary embodiments of the left earphone 37 and the right earphone 39 include E-A-RTONE 3A and E-A-RTONE 5A insert earphones. In general, insert earphones include sound transmission tubes. One sound transmission tube is inserted into each ear canal of the test subject. A portion of the sound transmission tube that is inserted into the ear canal is surrounded by a sound insulating material. Output from the audio amplifier 35 is transmitted to a bone conduction transducer 38. An exemplary embodiment of the bone conduction transducer 38 is a Radio Ear B71 Vibrator.

Due to low power requirements of the remote unit 5, the audio amplifiers 34, 35, and 36 may be low voltage amplifiers having output noise levels too high for the audiometric testing. To overcome the output noise levels, each of the audio amplifiers 34, 35, and 36 is equipped with an output attenuator controlled by the DSP 24 via attenuator control lines 51, 52 and 53 respectively.

Figure 3C:
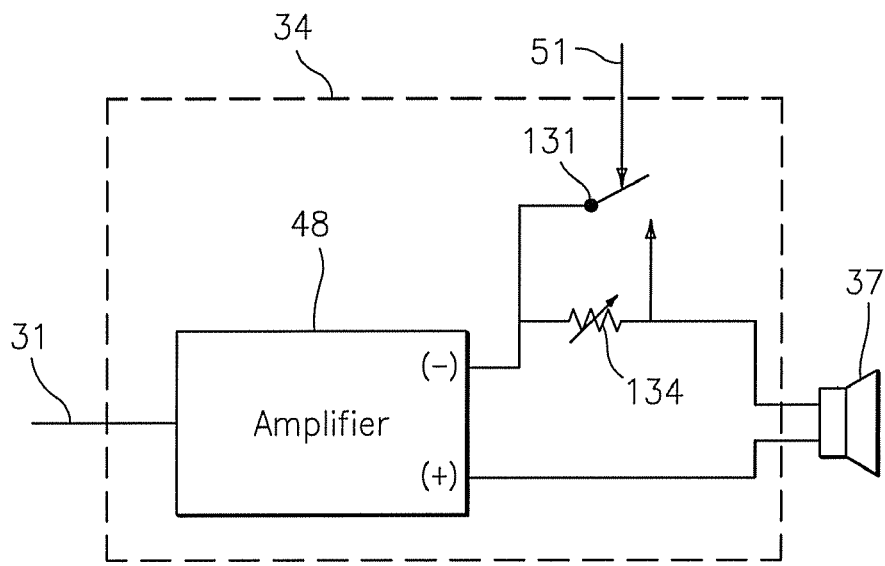
FIG. 3C illustrates an exemplary schematic diagram of an audio output amplifier.

FIG. 3C illustrates an exemplary schematic diagram of the audio amplifier 34. Similar schematic diagrams are also applicable to the audio amplifiers 35 and 36. The audio amplifier 34 includes an amplifier 48 such as a bridge-tied-load (BTL) amplifier. Exemplary embodiments of the amplifier 48 include a Texas Instruments TPA701. An analog switch 131 is controlled by the DSP 24 via the attenuator control line 51. When the analog switch 131 is closed, an output signal from the amplifier 48 is not attenuated. When the analog switch 131 is open, the output signal is attenuated by the ratio of resistance of a resistor 134 to an impedance of the left earphone 37. Typically, the resistor 134 will be set to reduce the level of the output signal by 30 db. In general, when the analog switch 131 is open, a level of signal at the input of the amplifier 48 will be amplified by the audiometer 9 by the same factor (i.e., 30 db) that the signal at the output of the amplifier 48 is attenuated. A result of amplification of digital audio signals before the DAC 26 and attenuation of analog signals after the amplifier 48 is that a level of an output signal from the audio amplifier 34 remains a nominal required test level but noise from the DAC 26 and the audio amplifier 48 is significantly reduced.

Figure 3D:
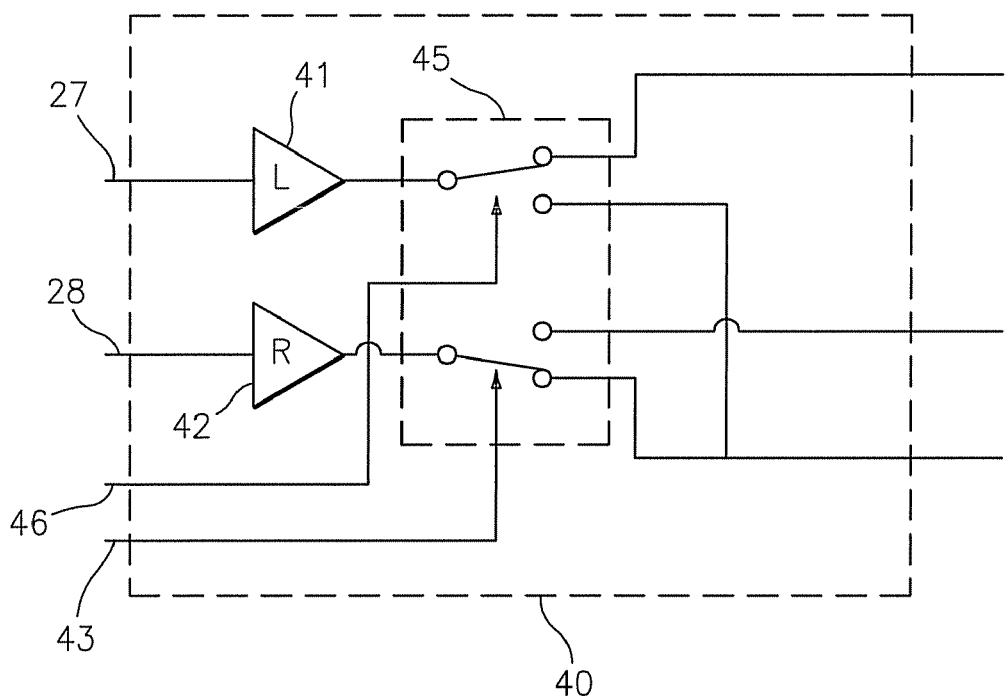
FIG. 3D illustrates an exemplary schematic diagram of a buffer and control block.

FIG. 3D illustrates an exemplary schematic diagram of the buffer and control block 40. The buffer and control block 40 is typically designed to route signals from two transmission channels into any two of three audiometric test channels.

Basic audiometric testing is generally performed monaurally, (i.e., right ear alone and left ear alone and levels are obtained separately from each test subject). No participation or influence from an opposite or "non-test" ear is intended. In certain instances and particularly where significant differences in sensitivity exist between the left and right ears, a better ear may perceive the test signal when a poorer ear is being tested. The response obtained from the test subject in that case would not be indicative of the hearing of an ear intended by the examiner. When an acoustic stimulus is presented at a high level to the poorer ear, there can be some unwanted transmission of part of that signal to the opposite ear. The unwanted transmission may be by air conduction due to leakage of sound around the ear cushions of the earphones, and even more so by way of bone conduction transmitted through the skull due to vibration from the earphone. Threshold differences of 40 dB or greater, (the interaural attenuation level for pure tone signals) can allow such "crossover" to occur when attempting to test the poorer ear. To eliminate the better ear's participation in the outcome of the test in these instances, sensitivity of the better ear must be temporarily reduced. Reducing the sensitivity of the better ear is accomplished by introducing a masking signal via air conduction to the better ear. In general, the masking signal is a narrow band noise (NBN) for pure tone testing. The masking signal is presented to the better ear while the poorer ear is being tested. Clinical masking requires calculation and adjustment of a masking level so that the masking level will prevent the detection of the acoustic stimulus by the non-test ear and yet not interfere with the detection of the acoustic stimulus in the ear under test.

Typically in case of bone conduction testing, the bone conduction transducer 38 is worn on the head (mastoid bone or other calibrated position) of the test subject stimulating both ears simultaneously. Both ears are stimulated with the test sounds. The ear that is not being tested is provided the masking signal via the earphones.

The digital audiometer 1 provides the masking signal for the non-test ear. Referring to FIG. 3A, the audiometer 1 transmits a "multiplexing mode" command to the DSP 11 via a control line 2. The DSP 11 transfers the multiplexing mode command to the first digital transceiver 12 via a first serial control interface 14. The first digital transceiver 12 transmits the multiplexing mode command to the second digital transceiver 22. The second digital transceiver 22 sends an "acknowledge message" back to the first digital transceiver 12. The acknowledge message acknowledges receipt of the multiplexing mode command. The multiplexing mode command is stored in a memory register that is accessible to the DSP 24 via a second serial control interface 20. The first serial control interface 14 and the second serial control interface 20 may be implemented by standard industry protocols such as serial peripheral interface bus (SPI), 2-Wire, and inter-integrated circuit (I2C). Referring to FIG. 3D, the DSP 24 controls a de-multiplexer 45 via control signals 43 and 46. The de-multiplexer 45 includes at least two analog switches or relays. The de-multiplexer 45 routes the left audio output signal 27 and the right audio output signal 28 to any two of the three audio amplifiers 34, 35, and 36.

Referring to FIG. 3D, the left audio output signal 27 and the right audio output signal 28 from the DAC 26 are processed by low noise amplifiers 41 and 42 respectively. An exemplary embodiment of the low noise amplifiers 41 and 42 includes a Maxim MAX4775. The low noise amplifiers 41 and 42 function as signal conditioning buffers and may include an anti-aliasing filter for removing high frequency noise and alias from output of the DAC 26.

FIGS. 3E, 3F and 3G illustrate exemplary schematic diagrams of three positions of the de-multiplexer 45. FIG. 3E shows the de-multiplexer 45 in a Left phone+Right phone (L/R) mode. In the L/R mode, any one of the ears of the test subject may be masked. FIG. 3F shows the de-multiplexer 45 in a Left phone+Bone Conduction (L/BC) mode. In the L/BC mode, the left ear of the test subject is masked. FIG. 3G shows the de-multiplexer 45 in a Right phone+Bone Conduction (R/BC) mode. In the R/BC mode, the right ear of the test subject is masked.

In another embodiment of the digital wireless interface 10, an audiometer with analog outputs provides analog input signals to the base unit. The audiometer with analog outputs is referred to as an "analog audiometer." In conventional operation, the analog audiometer provides analog electrical signals to the earphones worn by the test subject. The earphones transform the analog electrical signals to the test sounds.

Figure 4A:
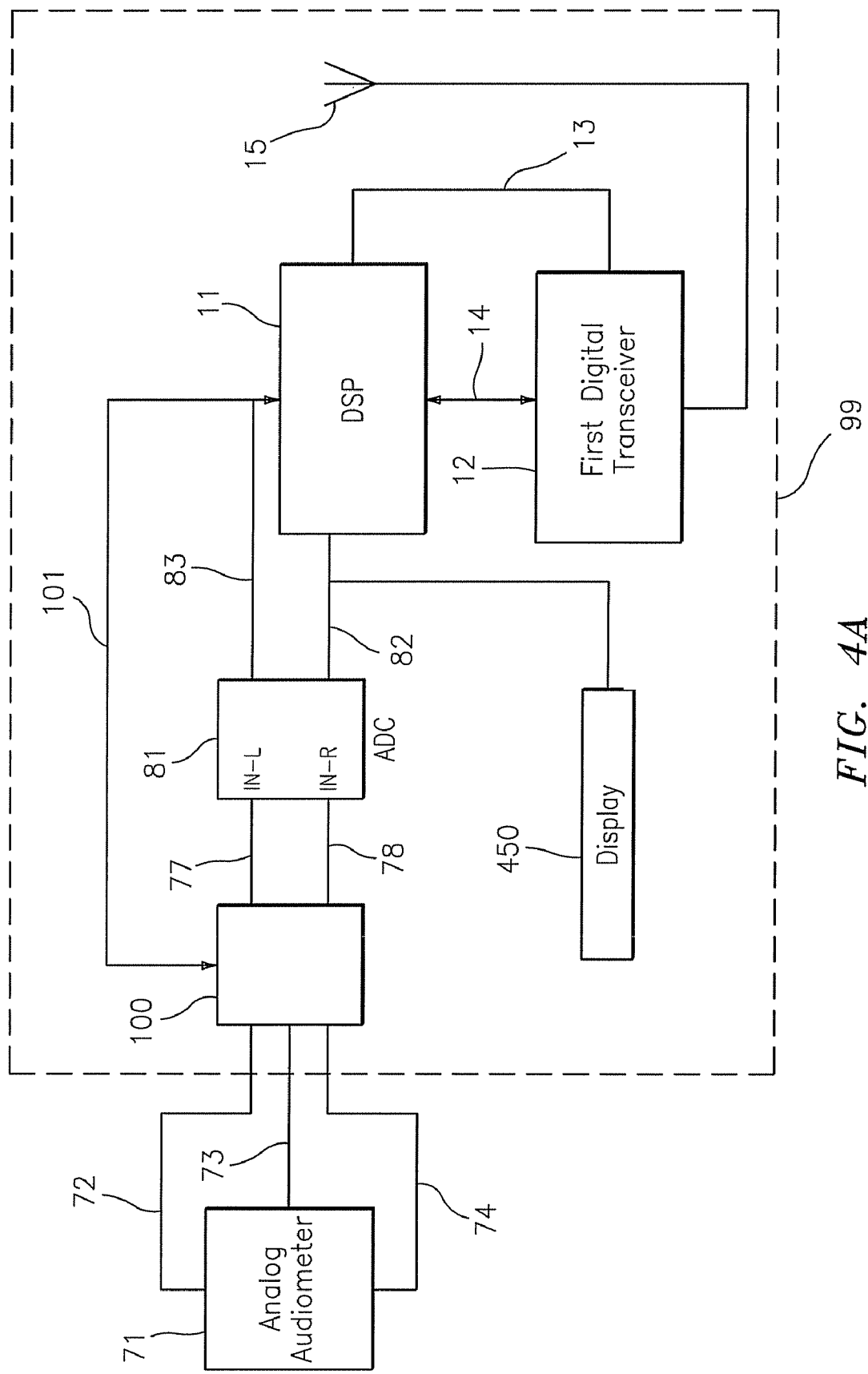
FIG. 4A illustrates an exemplary schematic diagram of an analog base unit.

FIG. 4A illustrates an embodiment of an analog input base unit 99 for connecting to an analog audiometer 71. A left channel analog audio signal 72 provides an analog signal related to the test sound intended for the left earphone 37. Similarly, a bone conduction channel analog audio signal 73 and a right channel analog audio signal 74 provide analog signals related to the test sounds intended for the bone conductor transducer 38 and the right earphone 39 respectively. The left channel analog audio signal 72, the bone conduction channel analog audio signal 73, and the right channel analog audio signal 74 are transmitted to a signal conditioning and multiplexing block 100. The signal conditioning and multiplexing block 100 multiplexes any two of three inputs, the left channel analog audio signal 72, the bone conduction channel analog audio signal 73, and the right channel analog audio signal 74 (collectively referred to as audio analog signals 72, 73, and 74) into a first audio analog channel 77 and a second audio analog channel 78. The first audio analog channel 77 is transmitted to a left input of a high resolution stereo analog to digital converter (ADC) 81. The second audio analog channel 78 is transmitted to a right input of the ADC 81. One exemplary embodiment of the ADC 81 is a Cirrus Logic CS5381. The ADC 81 converts the first audio analog channel 77 and the second audio analog channel 78 to a twenty-four bit stereo digital audio stream 82. The twenty-four bit stereo digital audio stream 82 typically has a sampling rate of 16 KHz or higher because the audiometers typically test up to 8 KHz. An exemplary embodiment of the format of the twenty-four bit stereo digital audio stream 82 is I2S. The twenty-four bit stereo digital audio stream 82 is transmitted to the DSP 11. The DSP 11 processes the twenty-four bit stereo digital audio stream 82 for transmission by the first digital transceiver 12 as described above with reference to FIG. 3A.

FIG. 4B illustrates an exemplary schematic diagram of the signal conditioning and multiplexing block 100. The twenty-four bit stereo digital audio stream 82 is designed to address certain issues associated with conversion of the audio analog signals 72, 73, and 74 over a wide dynamic range to the twenty-four bit stereo digital audio stream 82.

Unwanted sounds from the analog audiometer 71 should be −10 dB HL. The audio analog signals 72, 73, and 74 from some audiometers 71 may be as low as 200 nanoVrms at 1 KHz. Typically, the twenty-four bit stereo digital audio stream 82 is not designed to process signals below 1 µV. In general, the ADC 81 is specified at 120 db SNR. A maximum input into the ADC 81 is typically 2 Vrms. A corresponding minimum signal level is 2 µVrms. Therefore, the lowest signal from the analog audiometer 71 may need to be amplified by a factor of 10 just to exceed a noise floor of the ADC 81.

The analog audio signals 72 and 74 may be of a level below 1 µV. Referring to FIG. 4B, any two of the three analog audio signals 72, 73 and 74 are routed into two signal conditioning channels via multiplexer 120. The left channel analog audio signal 72 is transmitted to a first impedance matching and audio transformer block 111. The right channel analog audio signal 74 may be routed to the first impedance matching and audio transformer block 111 or to a second impedance matching and audio transformer block 112. The bone conduction channel analog audio signal 73 is routed to the impedance matching and audio transformer block 112. The first impedance matching and audio transformer block 111 and the second impedance matching and audio transformer block 112 each include an impedance matching circuit and an audio transformer. One exemplary embodiment of the audio transformer is a Jensen 13k6c. Audio transformers may add up to 26 db of gain (20 times) without adding significant noise or distortions.

The output of the first impedance matching and audio transformer block 111 is transmitted to a first low noise amplifier 115. The output of the second impedance matching and attenuator block 112 is transmitted to a second low noise amplifier 116. The first and second low noise amplifiers are collectively referred to as the low noise amplifiers 115 and 116. Exemplary embodiments of the low noise amplifiers 115 and 116 are Linear Technology LT1115.

The bone conduction channel analog audio signal 73 (related to the bone conduction transducer 38) may have a signal level as much as 40 db higher than the left channel analog audio signal 72 and the right channel analog audio output signal 74. The gain of amplifier 116 may be attenuated via control line 103 from DSP 11 to adjust the level of the bone conduction channel analog audio signal 73 to the range of the left channel analog audio signal 72 and the right channel analog audio signal 74.

For low levels of the analog audio signals 72 and 74, typically corresponding to air conduction test signals below 80 dB HL in a frequency range of 250-6000 Hz (referred to as a low state), the gain of the low noise amplifiers 115 and 116 is approximately 30 dB. Correspondingly, output of each of the audio output amplifiers 34 and 36 is typically attenuated by 30 dB. For high levels of the analog audio signals 72 and 74, typically corresponding to a range of 80-110 dB HL in the frequency range 250-6000 Hz (referred to as a high state), the gain of the low noise amplifiers 115 and 116 is approximately 0 db. Correspondingly, the output of each of the audio amplifiers 34 and 36 is typically not attenuated.

The gain of each of the low noise amplifiers 115 and 116 is controlled by the DSP 11 via gain control lines 102 and 103 respectively. The DSP 11 also controls the attenuation of the audio amplifiers 34 and 36 via the wireless link to the DSP 24. The DSP 24 uses the attenuator control lines 51 and 53 to control the attenuation of the audio amplifiers 34 and 36 respectively.

The DSP 11 determines one of the high state and the low state for the analog audio signals 72 and 74 by comparing the levels of the digital audio at the output of the ADC 81 corresponding with analog audio signals 72 and 74 to preset numeric thresholds.

A purpose of an upper threshold "$U_{TH}$" is to avoid "digital data overflow." The digital data overflow corresponding to the analog audio signals 72 and 74 is avoided by entering the high state when $U_{TH}$ is exceeded for any of the analog audio channels 72 and 74. Correspondingly, output of the audio amplifiers 34 and 36 respectively is attenuated. An electrical value corresponding to $U_{TH}$ is approximately 1.75 dB below an electrical value corresponding to full scale of the ADC 81. For example, if the full scale of the ADC 81 corresponds to an input signal of 5.6 V (peak-to-peak), then the electrical value corresponding to $U_{TH}$ is approximately 4.6 V (peak-to-peak).

To reduce computational load in the DSP 11, the data for determining the state of the levels of the analog audio signals 72 and 74 may be acquired as follows. The DSP 11 separates data from the ADC 81 into left channel words and right channel words based on input from an I2S word select clock. The DSP 11 truncates twenty-four bit words to eight MSB (most significant bits) to produce an eight-bit word. To reduce a quantization error, the DSP 11 may round a lower sixteen bits of the twenty-four bit words by adding 0x8000 before truncating. The DSP 11 derives an absolute value of the eight-bit words by activating the "ABS" instruction (or negate a value of the eight-bit word and add 1 when the value is negative). A stream of eight-bit words is created with decimal values between 0 and 127 for left channel words and right channel words. Respectively, $U_{TH}$ has an integer value of 103.

A purpose of a lower threshold "$L_{TH}$" is to improve the SNR across the wireless audiometric system 10. The SNR is improved by entering the low state, increasing the gain of low noise amplifiers 115 and 116 and attenuating the output of the audio amplifiers 34 and 36 by an inverse of the gain factor.

Figure 5:
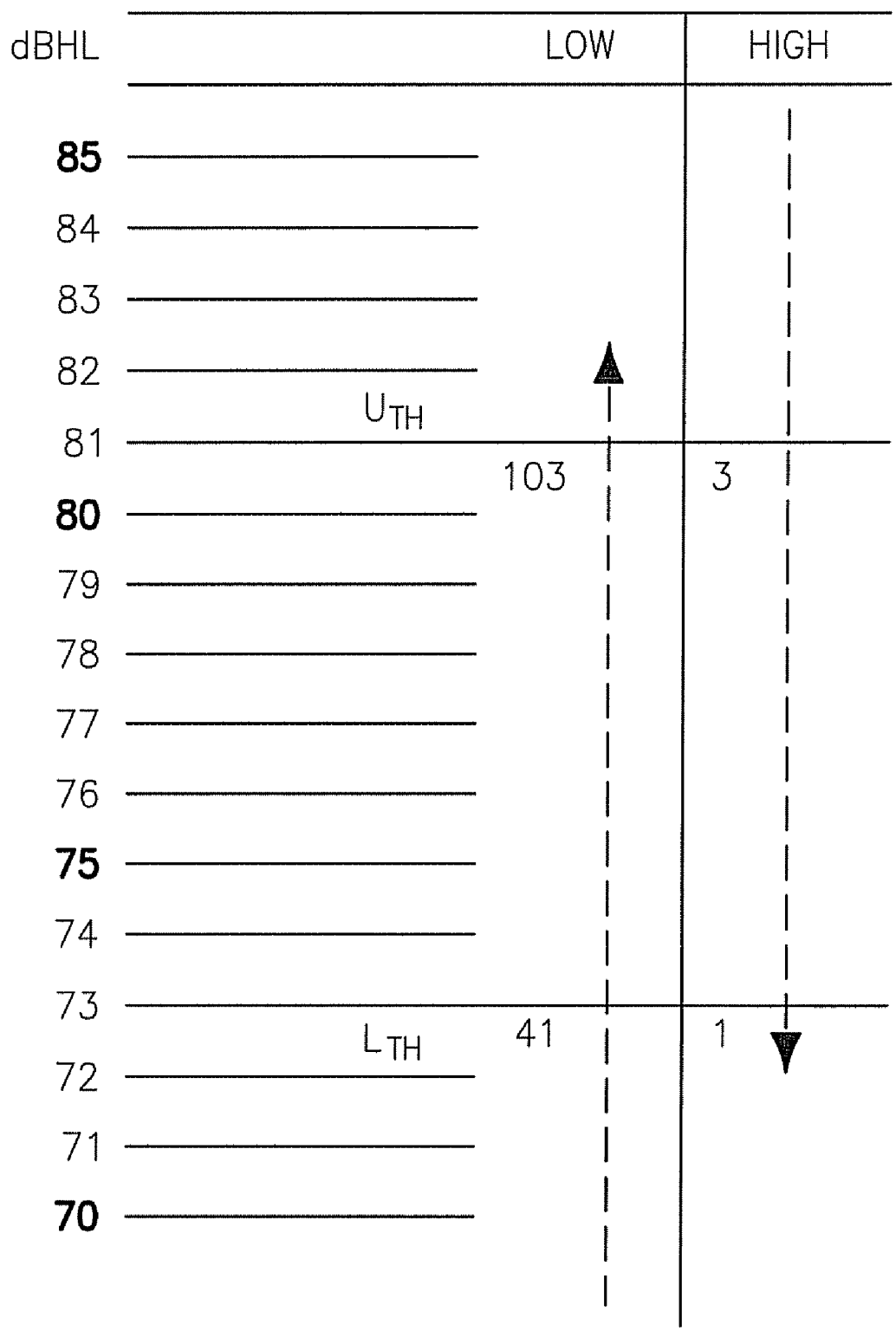
FIG. 5 illustrates an exemplary comparison of an upper threshold to a lower threshold.

FIG. 5 illustrates an exemplary comparison of the $U_{TH}$ to the $L_{TH}$. As shown in FIG. 5, the $L_{TH}$ is approximately 38 dB below the $U_{TH}$. The 38 dB is accounted for due to the 30 dB input gain difference between the low state and the high state plus 6 to 9 dB for hysteresis to prevent unnecessary fluctuations between the two states. Audiometer HL values corresponding with the thresholds are shown on the left side of FIG. 5 and the decimal values corresponding with $U_{TH}$ and $L_{TH}$ thresholds are shown on the right side of FIG. 5. A decimal value of the $L_{TH}$ is an integer with a value of 1. The vertical dashed arrow pointing upwards represents the absolute value of a digital signal processed by the DSP 11 in the low state. When the output equals a decimal integer value of 103 (corresponding with the audiometer's hearing level of 81 db HL and an analog signal level of 4.6 Vp-p at an input to the ADC 81), the output crosses the upper threshold $U_{TH}$. The state changes to the high state. The vertical dashed arrow pointing downward represents the absolute value of the digital signal processed by DSP 11 in the high state. In the high state the input to ADC 81 is reduced by –30 dB (1/31.6). As a result of the high state, the decimal integer value corresponding with $U_{TH}$ becomes 3 (103/31.6=3.3). The lower threshold $L_{TH}$ is 8 dB below $U_{TH}$, corresponding with a decimal integer value of 1. When the examiner reduces the level of the signal from the audiometer more than 8 dB HL to 73 dB HL, the decimal integer value becomes less than 1 (3/2.5=1.2) and the output crosses the lower threshold $L_{TH}$.

Figure 6:
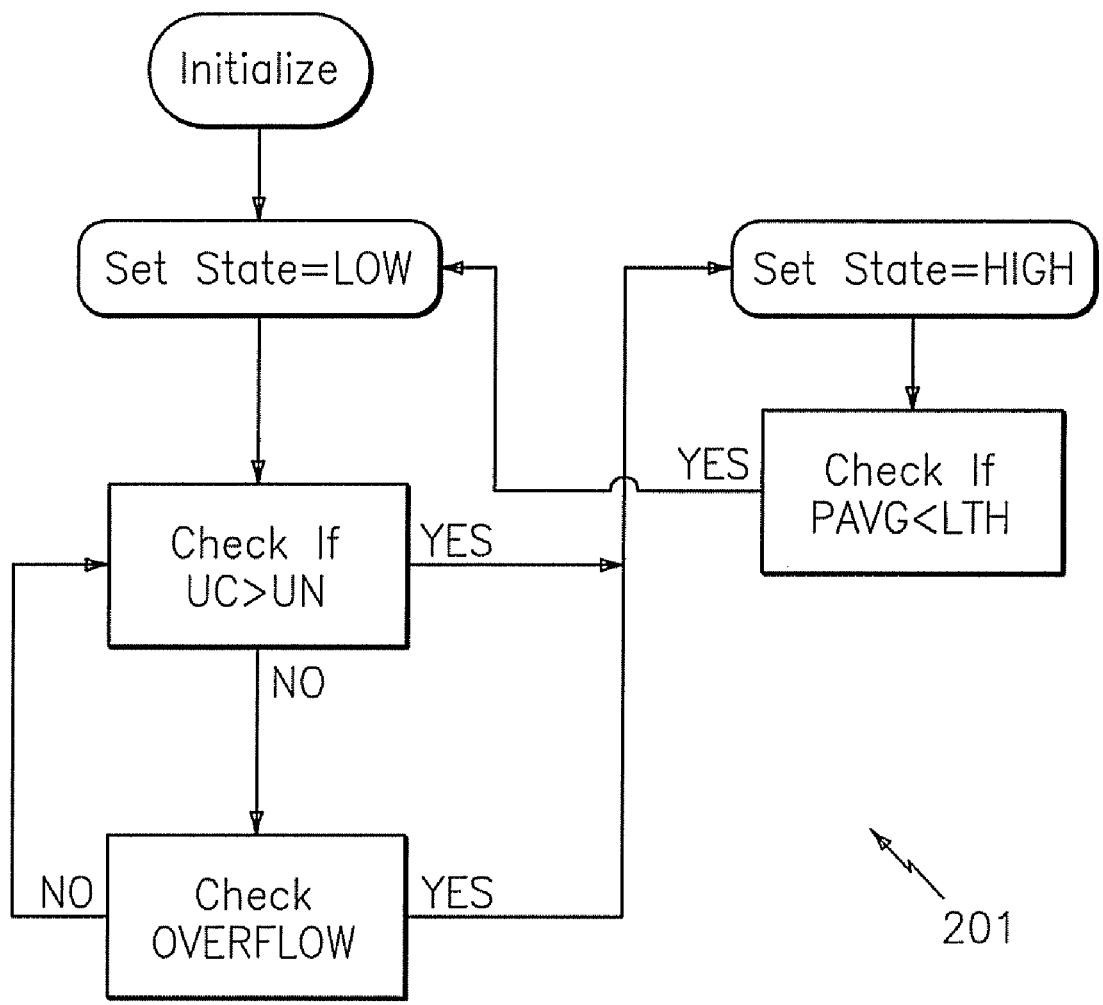
FIG. 6 illustrates an exemplary flow chart of an automatic scaling method.

FIG. 6 illustrates an exemplary flow diagram of an automatic scaling method 201. The automatic scaling method 201 provides for setting the low state and the high state. Referring to FIG. 6, a change from the low state to the high state is determined as follows. "$U_C$" is a number of times any of the absolute value of a digital signal processed by DSP 11 crosses the upper threshold $U_{TH}$ during a window with duration "$U_W$". The duration $U_W$ is typically several times longer than the cycle duration of the lowest test frequency. For example, if the lowest test frequency is 125 Hz, the cycle period is 8 mS. The duration $U_W$ is approximately 2 cycles (16 mS). The result $U_C$ is compared to a variable "$U_N$" which is a number selected to ensure an absolute value of the lowest test frequency signal will reach peak level during the duration $U_W$. For example, for $U_W$=16 mS, $U_N$ is a number between 1 and 2. When the $U_C$ is greater than the $U_N$, a change from the low state to the high state occurs. To minimize any delay for higher test frequencies, when $U_C > U_N$, the window is reset and the $U_C$ counting starts over. In case of data overflow during the low state, the DSP 11 initiates a change to the high state.

Referring to FIG. 6, a change from the high state to the low state is determined as follows. The DSP 11 selects peak values from the stream of 8 bit words. The DSP 11 averages the peak values during a window with duration "$L_W$." The duration $L_W$ is typically greater than 500 mS to ensure stable operation in case the test signal is speech. The result of the averaging is "$P_{AVG}$." The $P_{AVG}$ is compared to the lower threshold $L_{TH}$ that is approximately 38 dB below the upper threshold $U_{TH}$. When the $P_{AVG}$ is less than the $L_{TH}$, the DSP 11 initiates a change to the low state.

As long as the SNR of the ADC 81 and the DAC 26 combined is substantially above the SNR required from the analog audiometer 71, the automatic scaling method described above permits use of lower SNR and lower power ADCs and DACs. The lower SNR and lower power ADCs and DACs will accommodate the wide dynamic range of the analog audiometer 71. An exemplary embodiment of the lower SNR ADC is a Cirrus Logic CS5351. An exemplary embodiment of the lower SNR and lower power DAC is a Cirrus Logic CS4344. The automatic scaling method can be extended to include a plurality of graduated resealing steps. In a case of audiometric testing to test speech recognition, the graduated rescaling steps may have smaller decrements and increments to avoid any distortion of a speech signal.

Referring to FIG. 4B, the signal conditioning and multiplexing block 100 provides for multiplexing any two of the three analog audio signals 72, 73, and 74 into two signal conditioning channels resulting in the first audio analog channel 77 and the second audio analog channel 78 for masking purposes. The DSP 11 controls an input multiplexer 120 via the control bus 101 and multiplexer control signals 105 and 106. The input multiplexer 120 typically includes analog switches or relays.

FIGS. 4C, 4D, and 4E illustrate three exemplary multiplexing modes of the input multiplexer 120. FIG. 4D shows the input multiplexer 120 in the Left phone+Right phone (L/R) mode. In the L/R mode, anyone of the ears of the test subject may be tested or masked. FIG. 4E shows the input multiplexer 120 in the Left phone+Bone Conduction (L/BC) mode. In the L/BC mode, the left ear of the test subject is masked. FIG. 4F shows the input multiplexer 120 in the Right phone+Bone Conduction (R/BC) mode. In the R/BC mode, the right ear of the test subject is masked.

The DSP 11 controls the output de-multiplexer 45 via the wireless link to DSP 24 as illustrated in FIGS. 3D, 3E, 3F, and 3G.

The analog audiometer 71 does not provide any interface that could indicate to the DSP 11 a multiplexing mode. In a further embodiment of the signal conditioning and multiplexing block 100, a comparator block 118 (referring to FIG. 4B) and the DSP 11 are used to automatically detect the multiplexing mode.

Figure 7:
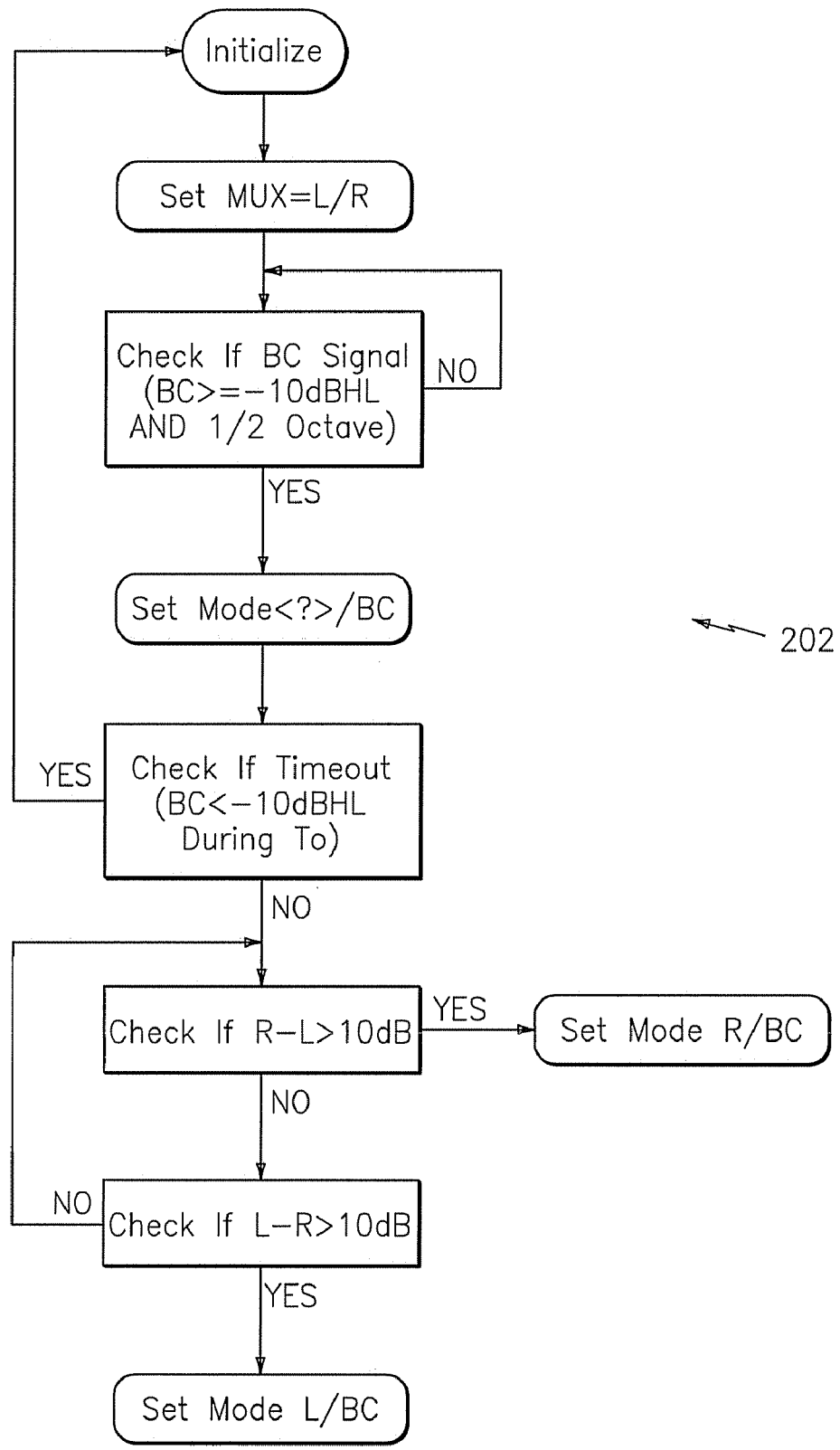
FIG. 7 illustrates an exemplary flow chart of an automatic multiplexing detection process.

FIG. 7 illustrates an exemplary flow chart of an automatic multiplexing detection process 202. A default mode of the input multiplexer 120 is the L/R mode. The comparator block 118 may include a precision comparator (such as an Analog Devices AD790) which can be set with a threshold higher than a noise level of the analog audiometer 9 and lower than a level of an electrical signal corresponding to the bone conduction channel analog audio signal 73 with a level of −10 dB HL. Thus when the analog audiometer 71 transmits a signal intended for the bone conduction transducer 38, the signal crosses the threshold respectively changing the logic state of a comparator output signal 109 from the comparator block 118. Because hearing tests using the bone conduction transducer 38 usually employ pure tones, the comparator output signal 109 will be a square wave with a frequency corresponding to the zero crossing of the pure tones.

The comparator output signal 109 is transmitted to a general purpose input on the DSP 11 via the control bus 101. Any comparator output signal 109 interrupts the DSP 11. The DSP 11 performs a zero-crossing frequency analysis on the comparator output signal 109 to determine the frequency of the pure tone. A number of times the comparator output signal 109 alternates between a low comparator state and the high comparator state in a time frame is counted. A zero crossing number is computed by averaging the number of times over several consecutive time frames. Since the analog audiometer 71 typically produces frequencies in ½ octave intervals, the zero crossing number can be compared to a lookup table. Thus, an accuracy of the zero crossing analysis is not critical. Therefore, the time frame and number of time frames can be reduced. The reduction in the time frame and the number of time frames results in a negligible delay of the DSP 11 controlling the output de-multiplexer 45.

The DSP 11 enters a "<?>/BC" mode upon detection of the comparator output signal 109 corresponding to a pure tone frequency used in audiometric testing. The pure tone frequencies are one of the ½ octave frequencies in the range 125-8000 Hz such as 125, 250, 500, 750, 1000, 1500, 2000, 3000, 4000, 6000, etc. In the <?>/BC mode, the DSP 11 determines which of the left earphone 37 and the right earphone 39 is used for masking.

During the <?>/BC mode, only a signal related to the bone conduction channel analog audio signal 73 is transmitted via the first digital transceiver 12 to the bone conductor transducer 38. In the <?>/BC mode, the DSP 11 creates a $4^{th}$ order digital band pass filter (BPF). Exemplary embodiments of the BPF include finite impulse response (FIR) or infinite impulse response filters (IIR). The BPF is centered geometrically around the frequency of the pure tone. The center frequency of the BPF is derived from the zero crossing analysis of the comparator output signal 109. The BPF has a bandwidth similar or narrower than a masking Narrow-Band Noise (NBN) from the analog audiometer 71. The values of the digital BPF signals related to the left channel analog audio signal 72 are compared to the values of the digital BPF signals related to the right channel analog audio signal 74 in an alternating fashion. The DSP 11 controls the input multiplexer 120 to alternate between the L/BC and the RIBC modes by toggling the state of control line 105. When the control line 105 is in a low state (0), a left input is routed to the ADC 81. When the control line 105 is in a high state (1), a right input is routed to the ADC 81. This alternates between the left and the right signals at the left channel input to ADC 81. During control line 105 low state, the DSP 24 averages output of the FIR or IIR and stores the average in memory as "BPF-LEFT." During control line 105 high state, the DSP 24 averages the output of the FIR or IIR and stores the average in memory as "BPF-RIGHT." A lowest level for masking corresponds with 0 dB HL. The noise of the audiometer is typically below −10 dB HL. Therefore, the value of the digital BPF signal corresponding with the channel carrying the masking signal is at least 10 dB greater than the value of the digital BPF signal for the channel not being used.

If the masking signal is detected by the DSP 11, the DSP 11 enters one of the L/BC mode and the R/BC mode corresponding to the masking signal. The DSP 11 also sets the input multiplexer 120 and the de-multiplexer 45 accordingly.

If no signal from the comparator block 118 is detected for more than a period $T_o$, then the DSP 11 will initialize the process and revert to the L/R mode as a default. The period $T_o$ may be a programmable variable, typically 30 seconds.

An alternative embodiment to the comparator in the comparator block 118 is a 16-bit analog to digital converter (referred to as ADC 118). A digital audio signal from the ADC 118 is transmitted to the DSP 11 via a standard digital audio format such as pulse-code modulation (PCM). Upon starting the analog audiometer 71, the DSP 11 momentarily samples the digital audio signal related to the bone conduction channel analog audio signal 73 to determine an average input noise level. Once the average input noise level is determined, the DSP 11 sets a noise threshold "$SN_{TH}$." When a level of the digital audio signal from the ADC 118 is greater than the noise threshold $SN_{TH}$, the DSP 11 determines a presence of signal at the analog audiometer 71 Bone Conduction output. A signal frequency and one of the analog audio signals 72 and 74 carrying the masking signal can be determined by the zero crossing frequency analysis on the digital audio signal from the comparator block 118 and a time domain filter on the masking signal.

Alternatively, to overcome the problem of signal detection in broad band noise, the DSP 11 can measure the noise in narrow bands corresponding with the ½ octave audiometric frequencies and assign a noise threshold for each frequency ($SN_{TH250}$, $SN_{TH500}$, etc). Any BC test signal from the audiometer will be detected in one of the narrow bands also indicating the test frequency. The narrow bands can be implemented as a time domain filter band, such as a series of IIR, using frequency domain analysis using a series of Discrete Fourier transforms (DFT) centered around the ½ octave audiometric frequencies or a computation of ½ octave bands from Fast Fourier transforms (FFT).

The different embodiments of the analog base unit 99 describe a configuration of multiplexing three analog audio signals into two (stereo) digital data conversion and transmission channels and de-multiplexing the two digital data transmission channels to three analog outputs as in FIG. 3B. The configuration is suggested because stereo digital audio protocols are standard on many readily available components. Also, a plurality of input/output channels may be transmitted via a plurality of signal processing and transmission channels.

Figure 8A:
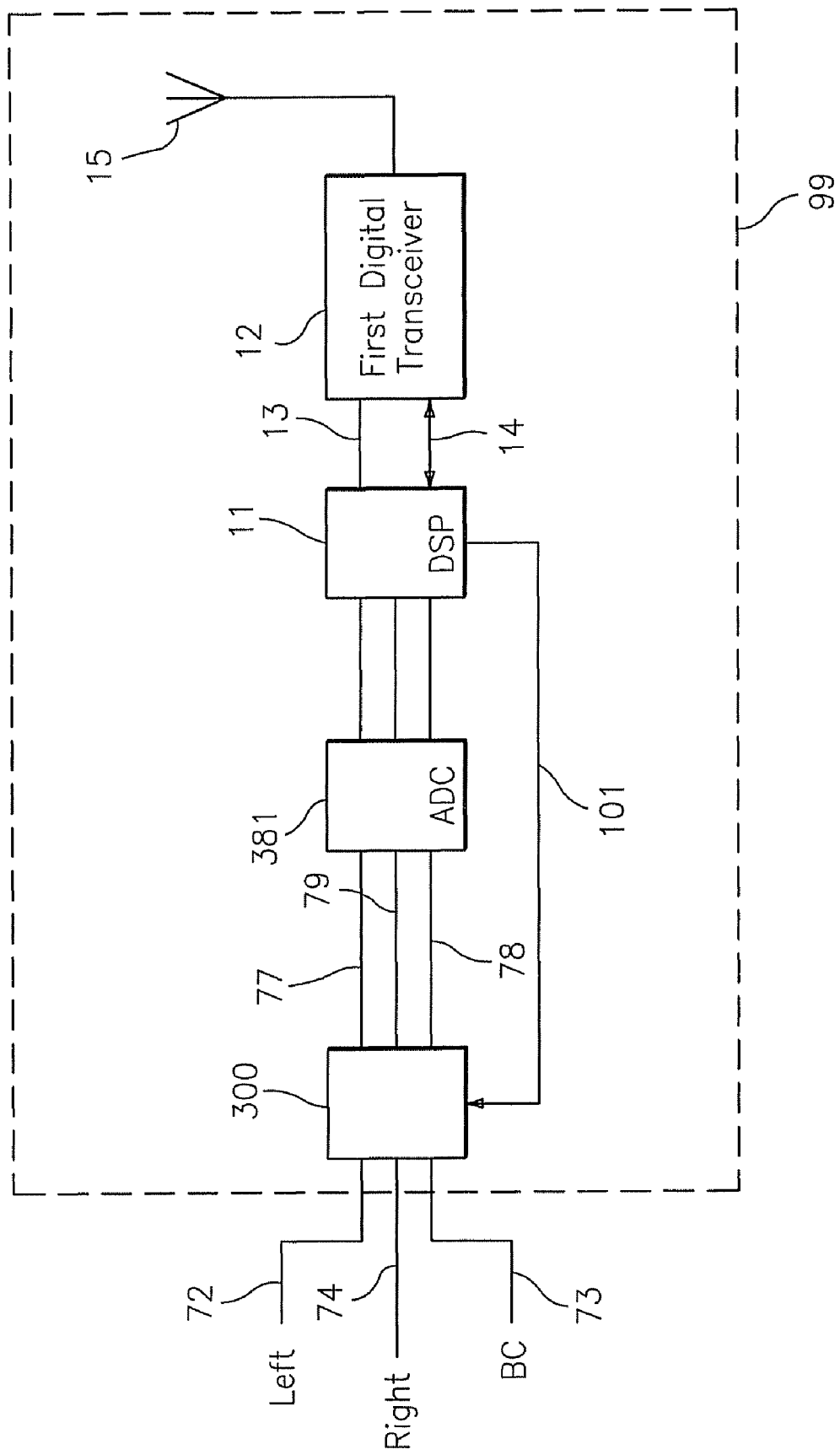
FIG. 8A illustrates an exemplary schematic diagram of another embodiment of the analog base unit.
Figure 8B:
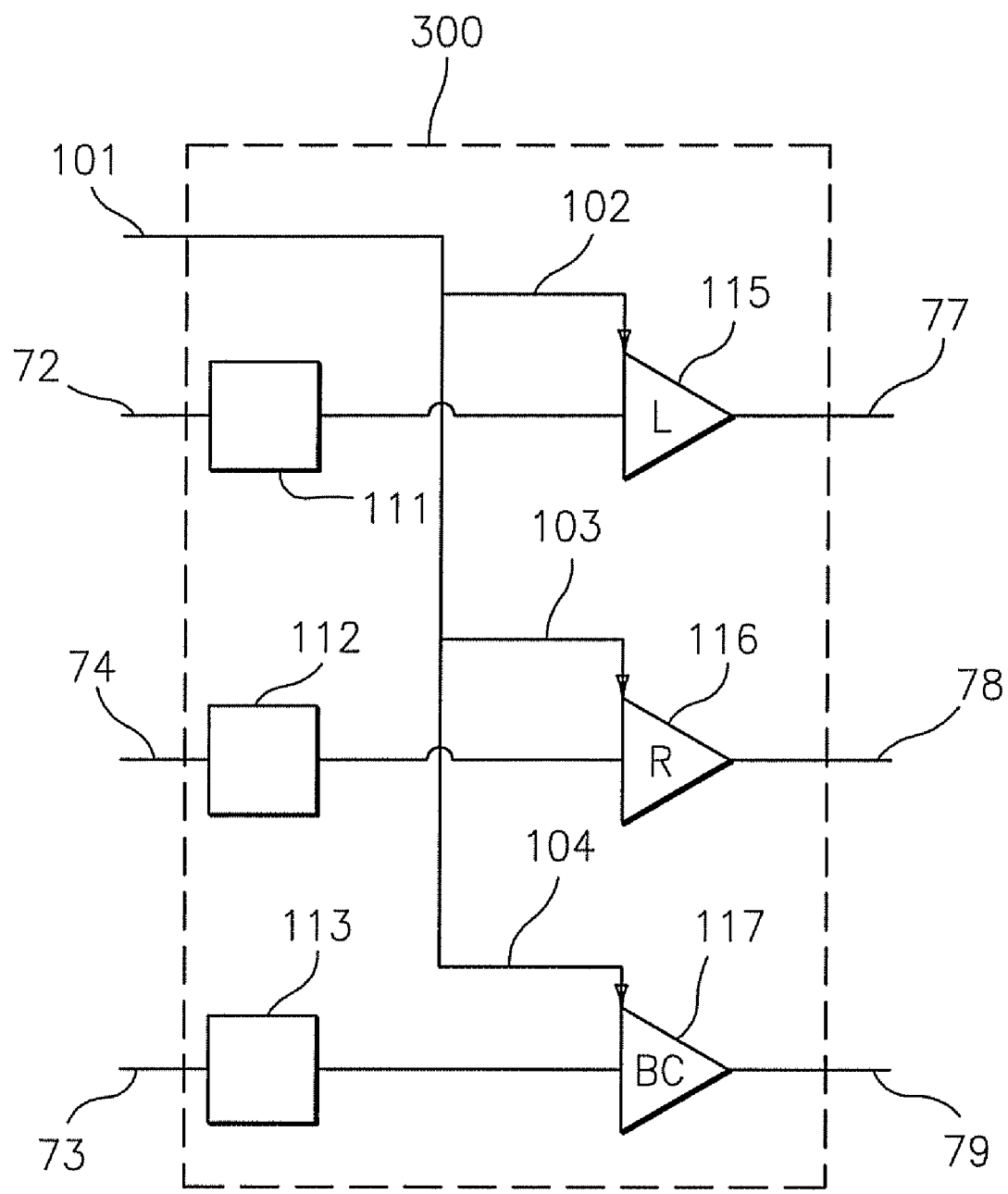
FIG. 8B illustrates an exemplary schematic diagram of a signal conditioner.
Figure 8C:
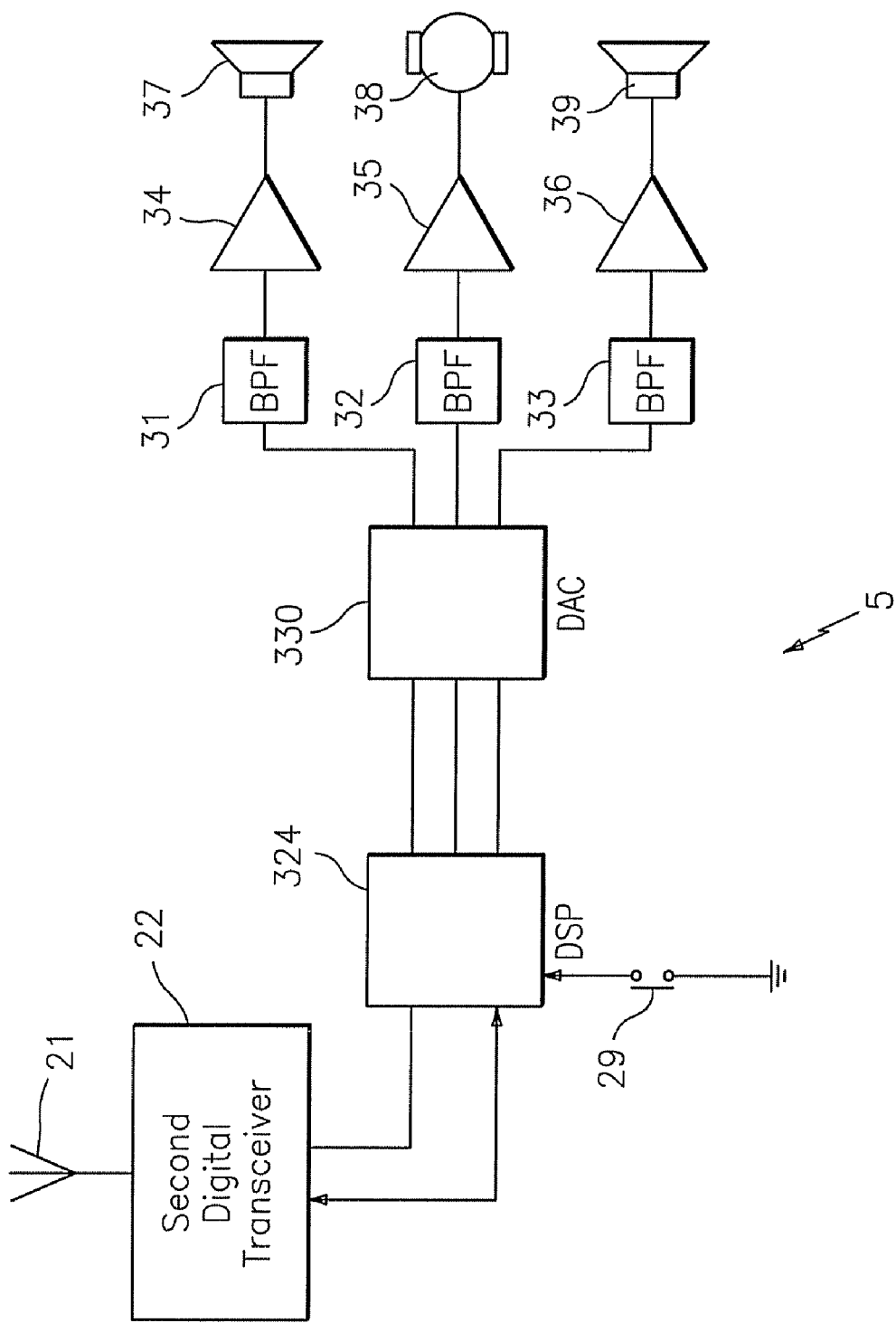
FIG. 8C illustrates an exemplary schematic diagram of another remote unit.

The analog base unit 99 may be implemented without the input multiplexer 120 that includes switches and relays. The digital wireless interface 10 may be implemented using a plurality of digital audio conversion and transmission channels. FIGS. 8A and 8B illustrate exemplary schematic diagrams of another embodiment of the analog base unit 99. FIG. 8A illustrates another exemplary schematic diagram of the analog base unit 99. The analog audio signals 72, 73, and 74 are input to a signal conditioner 300. The signal conditioner 300 does not include the multiplexer 120 included in the signal conditioner and multiplexer 100. FIG. 8B illustrates an exemplary schematic diagram of the signal conditioner 300. The signal conditioner 300 includes a gain control line 104, a third impedance matching and attenuator block 113, and a third low noise amplifier 117 among other components previously described. The output of the signal conditioner 300 includes the first audio analog channel 77, the second audio analog channel 78, and a third audio analog channel 79. The audio analog channels 77, 78, and 79 are input to an ADC 381. The ADC 381 converts the audio analog channels 77, 78, and 79 into three digital audio signals. The three digital audio signals are input to the DSP 11. The DSP 11 converts the three digital audio signals to a digital bit-stream. The first digital transceiver 12 transmits the digital bit-stream to the remote unit 5. FIG. 8C illustrates an exemplary embodiment of the remote unit 5. The digital bit-stream is received by the second digital transceiver 22. The digital bit-stream is input to a DSP 324. The DSP 324 converts the digital bit-stream into three digital audio channels. The three digital audio channels are input to a DAC 330. The DAC 330 converts the three digital audio channels into three analog audio channels. The three analog audio channels are input to the band pass filters 31, 32, and 33. The outputs of the band pass filters 31, 32, and 33 are processed as in FIG. 3B to produce the test sounds.

The digital wireless interface 10 further provides for calibrating sound pressure levels (SPL) of the test sounds to an ear canal of the test subject.

In order to obtain valid results, the audiometers 9 must be calibrated periodically. The calibration includes adjusting an intensity level at each selected frequency to meet a particular "Reference Equivalent Threshold Sound Pressure Level" (RETSPL) applicable to the type of the earphone being used. The RETSPL values were derived from SPL levels that correspond with an average hearing level sensation based on a population of adult subjects with normal hearing. In reality, test subjects may have ear canals with substantially different volume than the couplers used to establish the RETSPL (this difference is termed "real-ear to coupler difference" RECD) or the test subjects may suffer from a variety of disorders that could affect an SPL equivalency to hearing levels. Such discrepancy between the average derived from a normal hearing population and an individual test subject may result in a diagnostic error of up to 30 dB.

The digital wireless interface 10 provides for calibrating the sound pressure levels (SPL) of the test sounds to the ear canal of the test subject. Referring to FIG. 3B, a calibration block 400 provides for the calibrating. The calibration block 400 is connected to the DSP 24 via serial interface 401. FIG. 3H illustrates an exemplary schematic diagram of the calibration block 400.

Turning now to the left earphone 37 and the right earphone 39 (collectively referred to as insert earphones) used for the calibration, FIG. 9A illustrates an exemplary embodiment of an insert earphone tip 430. The insert earphone tip 430 provides for excluding ambient noise. Exemplary embodiments of the insert earphone tip 430 are an E-A-RLINK® 3A and an E-A-RLINK A5. The insert earphone tip 430 is inserted into the ear canal of the test subject. The insert earphone tip 430 includes a sound transmission tube 431. The sound transmission tube 431 introduces the test sounds into the ear canal of the test subject. A hole 426 is made in the insert earphone tip 430 approximately parallel to the sound transmission tube 431. An acoustic sensing tube 425 is inserted through the hole 426. The acoustic sensing tube 425 protrudes into the ear canal of the test subject. The examiner can adjust the length of the acoustic sensing tube 425 protruding into the ear canal for optimal proximity to a tympanic membrane in the ear canal. An exemplary material used for the acoustic sensing tube 425 is flexible silicon. FIG. 9B illustrates an exemplary embodiment of the acoustic sensing tube 425 connected to a first miniature microphone 415. Referring to FIG. 9B, the end of the acoustic sensing tube 425 that does not protrude into the ear canal is connected to a sound port of the first miniature microphone 415. Exemplary embodiments of the first miniature microphone 415 include Knowles Electronics FG series. Each of the insert earphones includes two insert earphone tips 430 (one for each ear) as described above. A second insert earphone tip is connected to a second miniature microphone 416 referred to in FIG. 3H. The first miniature microphone 415 and the second miniature microphones 416 are collectively referred to as the miniature microphones 415 and 416.

The audiometer 9 is calibrated via the wireless interface 10 to produce nominal sound pressure levels from the insert earphones. During a calibration procedure, the insert earphone is attached to an acoustic coupler (typically 2 cc for insert earphones) coupled to a sound level meter (SLM). Typically, the audiometer 9 is set at 70 dB HL and the calibration control of the audiometer 9 is adjusted to measure a sound pressure level (SPL) of 70 dBSPL+the RETSPL for the insert earphones at each calibration frequency. Next, calibration of the digital wireless interface 10 to the RETSPL is discussed in detail.

Following the calibration of the audiometer, the wireless system 10 is calibrated to reference calibration values (RCV). An example of a procedure for obtaining reference calibration values for the left earphone is discussed referring to FIG. 3H. With the earphone tip 430 still attached to the coupler and SLM, the miniature microphone 415 picks up acoustic signals from the coupler via the acoustic sensing tube 425 inserted into the coupler via hole 426. The DSP 24 transmits preset calibration signals via the path of DAC 26 and amplifier 34 to the left earphone 37. The left earphone 37 converts the preset electric calibration signals to calibration sounds. The calibration signals are typically of periodic nature such as impulse, sine bursts, chirp or noise bursts with integral number of cycles per frame. Another advantage of such broad band signals is reduction of the affect of interfering waves (i.e, standing waves). The miniature microphone 415 converts the sounds from the coupler to electrical signals. The electrical signals are amplified by a low noise amplifier 411. An exemplary embodiment of the low noise amplifier 411 is a Texas Instruments TL072. The amplifier 411 transmits an amplified signal to an ADC 410 that produces digital audio signals. An exemplary embodiment of the ADC 410 is an Analog Devices AD1870 16-bit Stereo ADC. The digital audio signals from ADC 410 are transmitted to the DSP 24 via the serial interface 401 such as I2S. The DSP 24 analyzes the response of the in the frequency domain by performing a Fast Fourier Transform (FFT). The DSP 24 has complete control of the period of the calibration signal and no windowing is necessary to prevent FFT leakage. A bandwidth (BW) of the Fourier transforms is centered on the audiometric test frequency. For example, if the sampling rate (Fs) is 16 KHz and an FFT bandwidth is 250 Hz, the FFT size (N) must be 32 points where:

$$N = \frac{Fs}{2*BW}.$$

Similarly, reference calibration values are obtained for the right earphone using a miniature microphone 416 and a low noise amplifier 412.

Results of the Fourier transforms are presented in bins corresponding to the FFT bands. The bin number represents a frequency. A bin number 1 represents the audiometric test frequency 250 Hz, a bin number 2 represents 500 Hz, a bin number 8 represents 2,000 Hz, etc. A level of the calibration sound in the coupler at a given frequency is related to the magnitude computed for the corresponding bin number.

The magnitude of the Fourier transform is calculated as the square root of a complex number. For example, using the FFT calculation, the magnitude of the transducer calibration signal related to the calibration sound in a given FFT band is calculated by:

$$\text{magnitude(band)} = \sqrt{FFT_{real}(band)^2 + FFT_{imag}(band)^2}$$

The magnitude for each audiometric test frequency corresponding with the calibration sound is stored in non-volatile memory (such as E2PROM) as a "reference calibration value" (RCV). Next, calibration of the digital wireless interface 10 to the test subject is discussed in detail.

At the beginning of an audiometric evaluation of the test subject, the system determines the deviation from a standard calibration. The DSP 24 produces preset calibration signals (same as during RCV calibration using the acoustic coupler) into the ear canals of the test subject via the left earphone 37 and the right earphone 39. The calibration of the left earphone 37 and the right earphone 39 for the test subject may be conducted simultaneously. Referring to FIG. 3H, the miniature microphones 415 and 416 receive the calibration sounds via the acoustic sensing tubes 425. The miniature microphones 415 and 416 convert the calibration sounds to electrical signals. The electrical signals are amplified by low noise amplifiers 411 and 412. The outputs of the low noise amplifiers 411 and 412 are transmitted to an ADC 410 that produces digital audio signals. The digital audio signals are transmitted to the DSP 24 via a serial interface such as I2S. The DSP 24 analyzes the digital audio signals. The DSP 24 performs a frequency analysis on the digital audio signals corresponding with calibration signals measured in the ear canal.

A test signal magnitude (TSM) is compared to the RCV in each audiometric test frequency. A ratio between the test signal magnitude and the RCV determines a deviation $\Delta_{RETSPL}$ of the individual ear from the RETSPL. The deviation can be expressed in decibels: $LOG_{10}(RCV/TSM)*20 = \Delta_{dBSPL}$. The deviation expressed in decibels is equivalent to a real ear to coupler difference (RECD) for the test frequency.

The $\Delta_{dBSPL}$, the test frequency, and ear identification is transmitted to the DSP 11 in the base unit 5. The $\Delta_{dBSPL}$, the test frequency, and ear identification may be sent in a format such as $\Delta_{dBSPL}$/EAR/FREQ (for example, 5 dB/LEFT/1000 Hz). In embodiments including the digital audiometer 1, the DSP 11 transmits the $\Delta_{dBSPL}$, the test frequency, and the ear identification to the digital audiometer 1. The digital audiometer 1 automatically corrects a signal (transmitted via the serial digital interface 3) corresponding to the deviation. The deviations can be stored for the test subjects in a memory with the digital audiometer 1 (or the computer-processing unit as disclosed above). In embodiments including the analog audiometer 71, the $\Delta_{dBSPL}$, the test frequency, and ear identification information is presented to the examiner via a user interface 450 (referring to FIG. 4A). Typically, the user interface 450 includes at least one of an LCD and an LED display incorporated in the analog base unit 99 visible to the examiner. The examiner can correct for the ears of the test subject by offsetting the left channel analog audio signal 72 and the right channel analog audio signal 74.

Further analysis of the test signals and test conditions may be available using of the elements and method described above for ear canal measurements.

The digital wireless interface 10 may provide for determining a correct placement of the insert earphone tip 430 and the acoustic sensing tube 425 in the in the ear canal of the test subject. The DSP 24 may produce a broadband signal into a center of the ear canal via the sound transmission tube 431 in the center of the insert earphone tip 430. The DSP 24 measures an acoustic signal in the ear canals via the acoustic sensing tubes 425 and the calibration block 400. The DSP 24 performs a magnitude analysis on the acoustic signal to determine a frequency response for the ear canal. The result of the magnitude analysis can be compared to a "correct placement response." For example, a roll-off in the high frequencies may indicate incorrect placement of the acoustic sensing tube 425. In the case of certain deviations from the correct placement response, the DSP 24 alerts the examiner to adjust the position of the acoustic sensing tube 425.

Phase information may also be a product of the frequency domain analysis of the acoustic signal. A phase is calculated from the complex number resulting from the Fourier transform calculation. For example, using the FFT:

$$\text{phase(band)} = \tan^{-1}\left(\frac{FFT_{imag}(\text{band})}{FFT_{real}(\text{band})}\right) \text{ for } 0 < \text{angle} < 90$$

The phase information derived from the frequency domain analysis is compared with the phase of the electrical signal to the left earphone 37 and the right earphone 39. A difference between the phases (Δphase) is used to estimate effects of interfering waves (i.e., standing waves).

The digital wireless interface 10 may also be used to determine if ambient noise in a test environment exceeds permissible levels. While the ear canal is occluded by the insert earphone tip 430, the DSP 24 may mute the output from the DAC 26 and measure the acoustic signal in the ear canal via the acoustic sensing tube 425 and the calibration block 400. The DSP 24 performs the frequency domain analysis on a signal selected by the calibration block 400. From the frequency domain analysis, the frequency and level of the ambient noise in the ear canals are determined. The frequency and level of the ambient noise are then compared to a preset table of acceptable noise levels in each frequency.

In case of high levels of ambient noise, the DSP 24 may transmit an alert signal to the DSP 11 in the base unit. The DSP 11 may display the alert signal to the examiner via a second serial digital interface 2 to the digital audiometer 1 (referring to FIG. 3A) or via the user interface 450 with the analog base unit 99 (referring to FIG. 4A).

Further, the digital wireless interface 10 may reduce an adverse affect of the ambient noise on audiometric test results. The DSP 11 may analyze phase characteristics of the ambient noise. From an analysis of the phase characteristics, the DSP 11 synthesizes an anti-phase signal to cancel the ambient noise. Typically, the DSP 11 synthesizes the anti-phase signal using an inverse FFT (IFFT). Alternatively, the DSP 24 may produce the anti-phase signal by implementing a finite impulse response (FIR) digital filter. In one embodiment, whenever an audiometric test sound is not produced, the DSP 24 may measure the ambient noise in the ear canal and update the anti-phase signal to cancel the ambient noise. The anti-phase signal is updated by applying an adaptive algorithm (such as least mean squares). The adaptive algorithm controls the coefficients of at least one of the FIR digital filter and phase parameters of the IFFT synthesis of the anti-phase signal.

Referring to FIGS. 3B and 7C, the remote unit 5 includes a response switch 29. The response switch 29 provides for communicating a response from the test subject to the examiner. In general, the test subject will push the response switch 29 upon recognizing the test sound.

Figure 10:
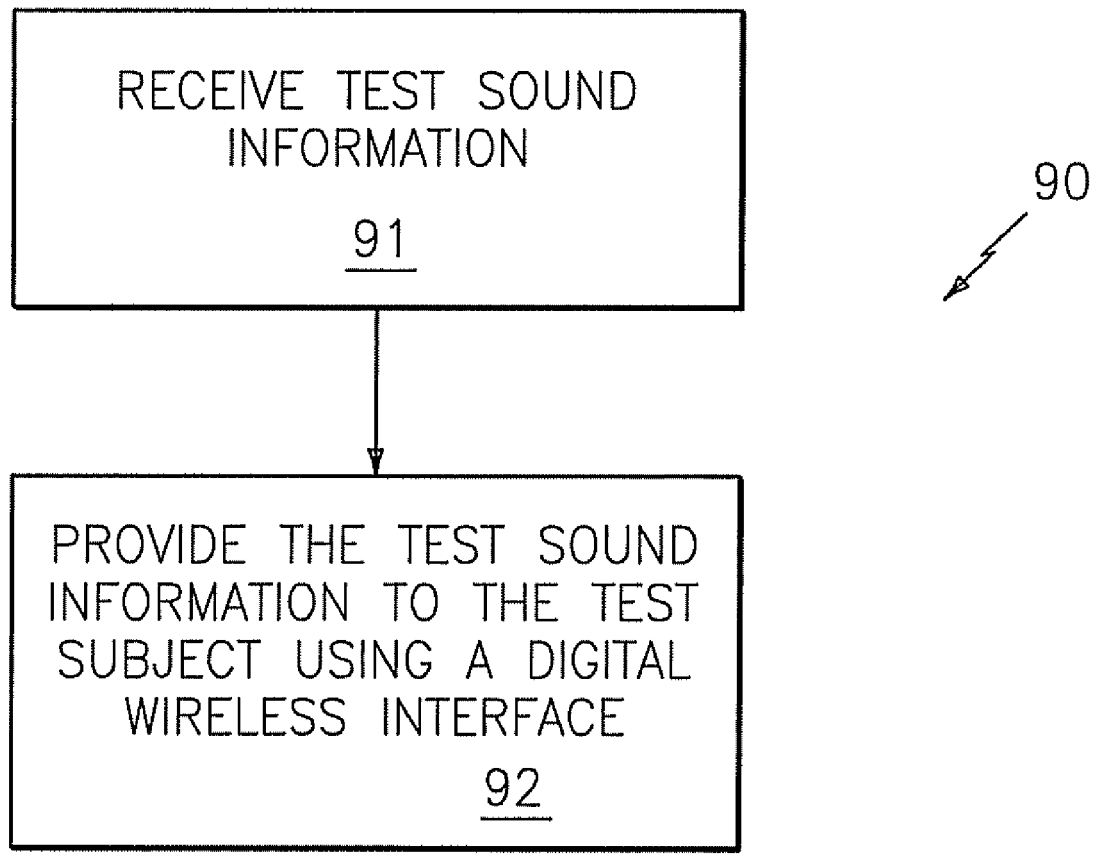
FIG. 10 illustrates an exemplary method for conducting an audiometric test.

FIG. 10 illustrates an exemplary method 90 for conducting an audiometric test. A first step 91 includes receiving the test sound information 7 from the audiometer 9. A second step 92 includes using the digital wireless interface 10 to provide the test sound information 7 to the test subject. Typically, the second step 92 includes converting the test sound information 7 to the test sounds 19. The second step 92 may also include transmitting a response from the test subject to the examiner via the digital wireless interface 10.

As one skilled in the art will recognize, the digital wireless interface 10 may exist in various embodiments. Some of the various embodiments are discussed in detail next.

Figure 11A:
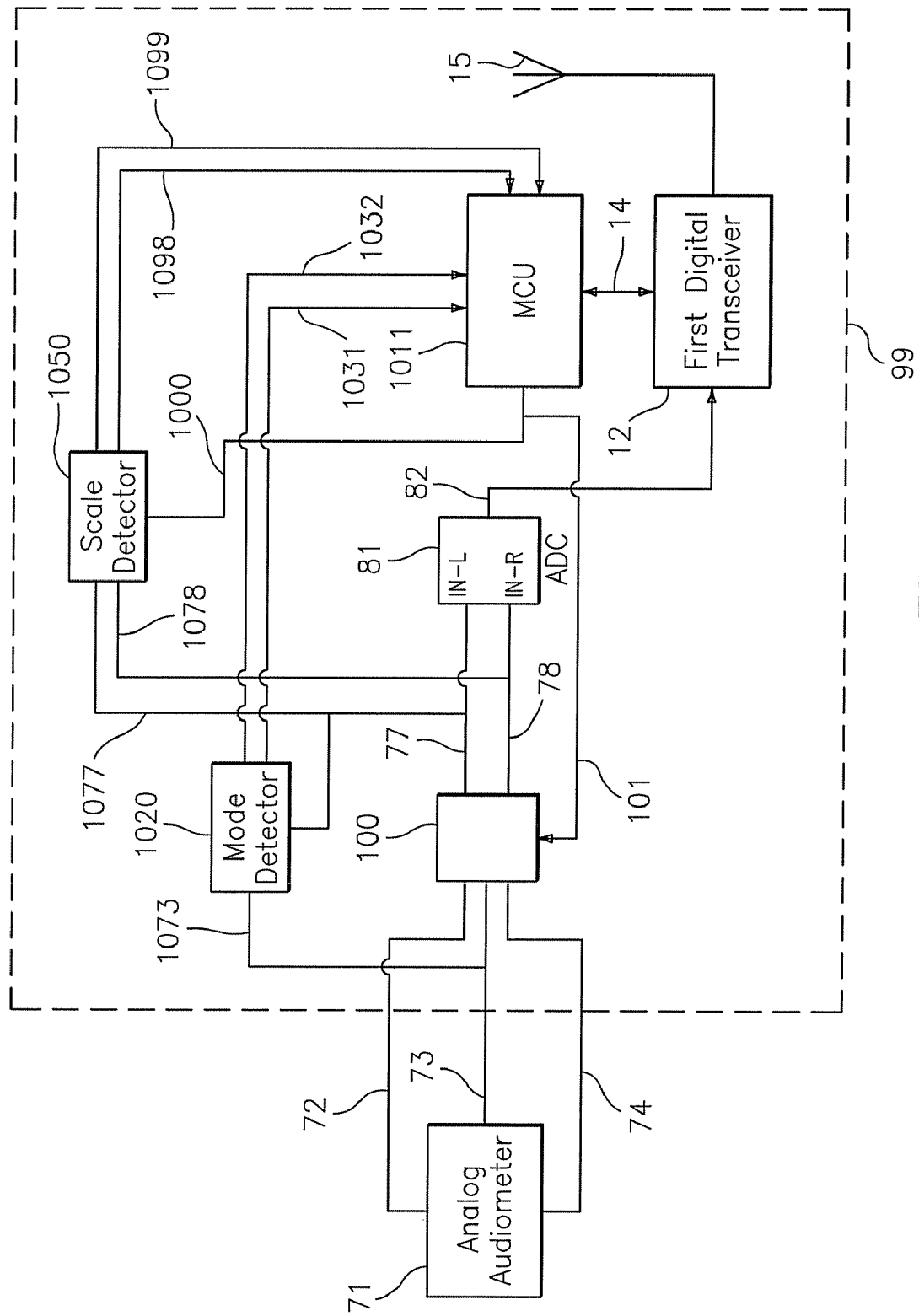
FIG. 11A illustrates an exemplary schematic diagram of another embodiment of the analog base unit.

An exemplary schematic diagram of another embodiment of the analog base unit 99 is illustrated in FIG. 11A. This embodiment replaces the DSP 11 with a micro-controller unit (MCU) 1011. Typically, the MCU 1011 may be of a general-purpose type MCU. In general, hardware detectors replace algorithms performed by the DSP 11. The MCU 1011 controls the analog base unit 99. The analog audio signals 72, 73, and 74 are processed in a manner similar to the manner discussed above with respect to FIG. 4A. A mode detector 1020 detects the presence of the analog audio signals 72, 73, and 74. For the analog audio signals 72, 73, and 74 that are present, the mode detector 1020 sends a logic level signal to the MCU 1011. The MCU 1011 controls the input multiplexer 120 and the de-multiplexer 45. A scale detector 1050 compares the first audio analog channel 77 and the second audio analog channel 78 to preset thresholds. The first audio analog channel 77 and the second audio analog channel 78 are input to the scale detector 1050 via channels 1077 and 1078 respectively. The scale detector 1050 provides logic level signals to the MCU 1011 for controlling a scaling process similar to the gain and attenuation control described above with respect to FIG. 4B.

Figure 11B:
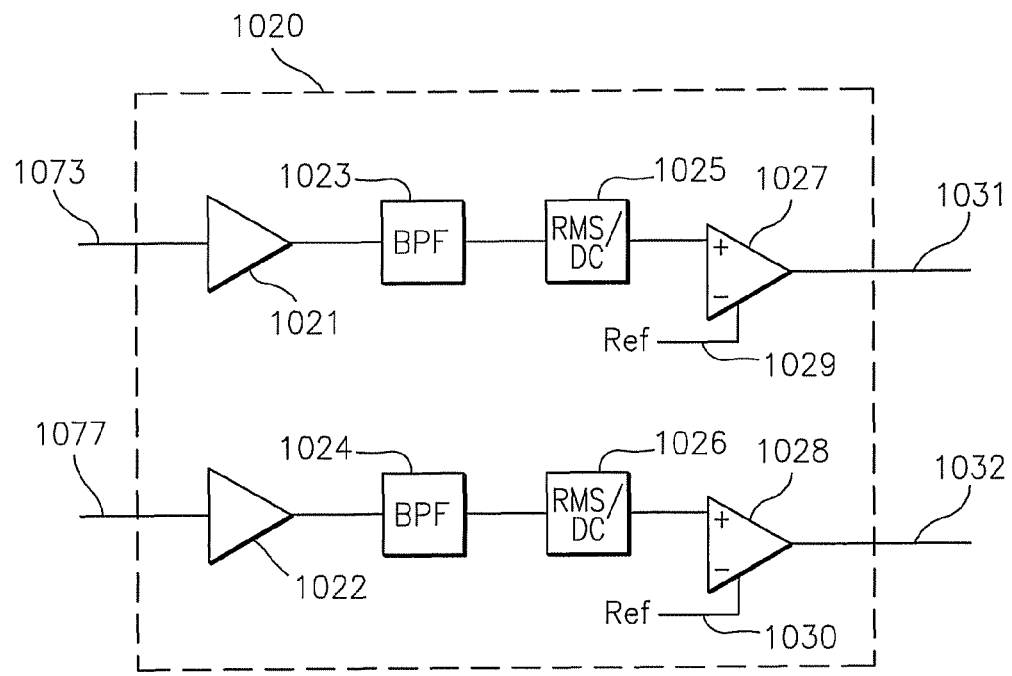
FIG. 11B illustrates an exemplary schematic diagram of a mode detector.

FIG. 11B illustrates an exemplary schematic diagram of the mode detector 1020. The mode detector 1020 includes two signal detector circuits, one for each of two inputs. Input signal 1073 is derived from the bone conduction channel analog audio signal 73. Input signal 1077 is derived from the first audio analog channel 77. Amplifiers 1021 and 1022 amplify the input signals 1073 and 1077 respectively to produce amplified signals. The amplified signals are processed by band pass filters (BPF) 1023 and 1024 to produce filtered signals. The BPF 1023 and 1024 accommodate levels of the analog audio signals 72, 73, and 74 that are typically higher in the lower and higher frequencies than the levels in the mid frequencies. The BPFs 1023 and 1026 each include a $2^{nd}$ order high pass filter (HPF) with a cutoff frequency of 750 Hz and a $2^{nd}$ order low pass filter (LPF) with a cutoff frequency of 4000 Hz. The LPFs and HPFs have a response that falls off sharply outside a pass band such as in a Chebyshev filter. A reduction in bandwidth provided by the BPFs 1023 and 1024 result in increased signal to noise ratio. In order to detect lowest levels of the analog audio signals 72, 73, and 74, the lowest levels and randomly fluctuating noise are averaged. The averaging ignores random noise peaks. The averaging is performed by RMS detectors 1025 and 1026. An exemplary embodiment of the RMS detectors 1025 and 1026 is a Linear Technology LTC1966 True RMS to DC Converter. DC output from the RMS detectors 1025 and 1026 is transmitted to comparators 1027 and 1028. Each of the comparators 1027 and 1028 includes a preset threshold corresponding with the lowest levels of the analog audio output signals 72, 73, and 74 but substantially above a noise level of the audiometer 9. The comparators 1027 and 1028 produce logic level signals 1031 and 1032 respectively. The logic level signals 1031 and 1032 may be one of a low level and a high level. The logic level signals 1031 and 1032 are transmitted to MCU 1011. When the analog audiometer 71 produces the analog audio output signals 72, 73, and 74, DC level signals from the RMS detectors 1025 and 1026 activate the comparators 1027 and 1028 to produce the logic level signals 1031 and 1032 at the high level. The MCU 1011 performs an automatic mode selection. The analog base unit 99 starts in a default mode to receive the left channel analog audio signal 72 and the right channel analog audio signal 74. When the analog audiometer 71 produces the bone conduction channel analog audio output signal 73, the bone conduction channel analog audio signal 73 is detected by the mode detector 1020. The mode detector 1020 produces the logic level signal 1031 with a high level. Correspondingly, the MCU 1011 enters the <?>/BC mode. In the <?>/BC mode, the MCU 1011 determines which of the left earphone 37 and the right earphone 39 is used for masking the test sounds to the ear canal of the test subject.

During the <?>/BC mode, only the signal related to the bone conduction channel analog audio signal 73 is transmitted to the remote unit 5. The MCU 1011 controls input multiplexer 120 to alternate between the L/BC and R/BC modes. When one of the left channel analog audio signal 72 and the right channel analog audio output signal 74 produces a masking narrow band noise, the mode detector 1020, via the input signal 1077, detects one of the left channel analog audio output signal 72 and the right channel analog audio signal 74. The comparator 1028 produces the logic level signal 1032 at the high level. By correlating the high level of the logic level signal 1032 with a position of the input multiplexer 120, the MCU 1011 determines which of the left channel analog audio signal 72 and the right channel analog audio signal 74 produces the masking narrow band noise. The MCU 1011 routes electrical signal related to the masking narrow band noise to one of the left earphone 37 and the right earphone 39 as appropriate.

If the bone conduction channel analog audio signal 73 is not detected in a time interval $T_0$ ($T_0$ may be a programmable variable, typically 30 seconds), the MCU 1011 will revert to the L/R mode as a default. The MCU 1011 will maintain the L/R mode until the bone conduction channel analog audio signal 73 is detected.

The audiometer 9 may be used for speech detection and recognition testing. Analog electrical signals related to sound waves resulting from speech may not be symmetrical. The analog electrical signals may be biased towards one of a negative side and a positive side. The root-mean-square (RMS) of the analog electrical signals is not correlated to positive or negative peak values that may be at least 15 db above a RMS value. Therefore, in order to detect the analog electrical signals corresponding to a full scale of the ADC 81, the scale detector 1050 provides both positive and negative peak detection.

Figure 11C:
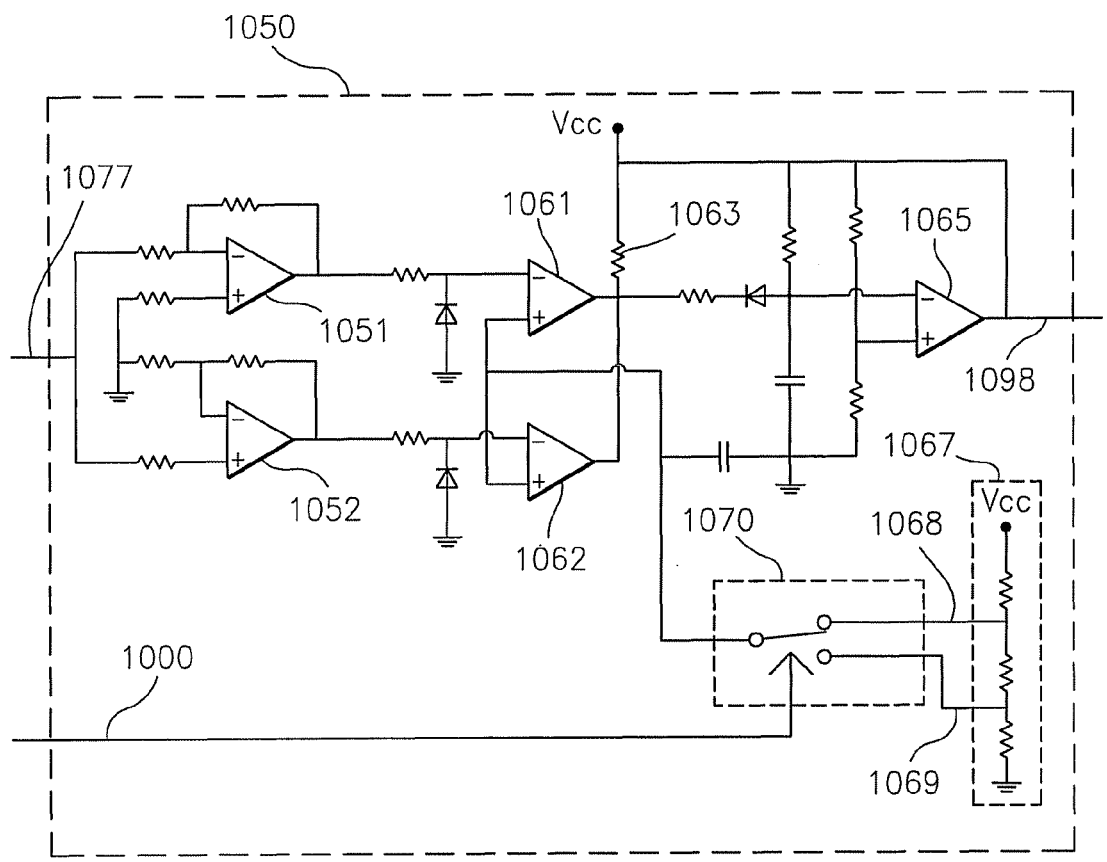
FIG. 11C illustrates an exemplary schematic diagram of a scale detector.

The scale detector 1050 includes two detection channels, one detection channel for the channel 1077 and one detection channel for the channel 1078. The following discussion applies to the detection channel for the channel 1077. A similar discussion applies to the detection channel for the channel 1078. FIG. 11C illustrates an exemplary embodiment of the scale detector 1050. The channel 1077 is transmitted to amplifiers 1051 and 1052. The amplifier 1051 is configured as an inverting follower while the amplifier 1052 is configured as a non-inverting follower. Outputs from the amplifiers 1051 and 1052 are transmitted to comparators 1061 and 1062 respectively via half wave rectifiers. Because the outputs of the amplifiers 1051 and 1052 are inverted with respect to each other, positive peaks at the output from the amplifier 1051 represent negative peaks of the channel 1077. Similarly, positive peaks from the output of the amplifier 1052 represent positive peaks of the channel 1077. The comparators 1061 and 1062 are open collector comparators. The comparators 1061 and 1062 are configured as inverting comparators. Because of the configuration of the comparators 1061 and 1062, the outputs of the comparators 1061 and 1062 may be connected together at a connection point. The connection point is connected to a voltage Vcc via a pull-up resistor 1063. The configuration of the comparators 1061 and 1062 creates a logic "OR" configuration. With the logic "OR" configuration, if any input to the comparators 1061 and 1062 is above the threshold of the comparators 1061 and 1062, then the output of both comparators 1061 and 1062 will be the low level. The comparators 1061 and 1062 have a common reference point. A resistor block 1067 includes a resistor network. The resistor network is supplied with the voltage Vcc. Typically, the voltage Vcc is provided by a regulated power supply. The resistor network 1067 produces a high reference DC level 1068 and a low reference level 1069. The high reference DC level 1067 corresponds to an upper threshold. The low reference DC level 1068 corresponds to a lower threshold. The high reference DC level 1067 and the low reference DC level 1068 are connected to a threshold analog switch 1070. Positions of the threshold analog switch 1070 are controlled by the MCU 1011 via a threshold control line 1000. One of the high reference DC level 1067 and the low reference DC level 1068 is connected to the common reference point of the comparators 1061 and 1062. By controlling the positions of the threshold analog switch 1070, the MCU 1011 sets the comparators 1061 and 1062 to actuate with respect to one of the upper threshold and the lower threshold.

When one of a positive and negative peak of the channel 1077 crosses a threshold set by the MCU 1011, common output of the comparators 1061 and 1062 goes to the low level. If peaks of the channel 1077 are close to the threshold, the duration of the low level may be short. Short durations of the low level may require a high sampling rate by the MCU 1011. Short durations of the low level result in short pulses. A comparator 1065 extends a series of short logic low pulses from comparators 1061 and 1062 to produce longer duration logic high level pulses. The comparator 1065 has a reference voltage that is typically one-half of Vcc. Typically, an inverting input to the comparator 1065 has a voltage level of Vcc. The comparator 1061 has an inverting configuration. Therefore, an output signal 1098 from the comparator 1065 is typically at a low state. When at least one of the comparators 1061 and 1062 detect a peak exceeding the threshold on the channel 1077, the common output of the comparators 1061 and 1062 goes to the low level. The low level of the common output discharges a capacitor on the inverting input to the comparator 1065 via a diode and resistor. A number or duration of pulses at the low level that will discharge the capacitor to a voltage below Vcc/2 (and the corresponding response time of the scale detector 1050) is adjustable. The number or duration of pulses is adjustable by a capacitor-resistor time constant. When the number of pulses discharges the capacitor below the reference voltage on the non-inverting input of the comparator 1065, the output signal 1098 is at a high state. The output signal 1098 at the high state is transmitted to the MCU 1011.

Figure 12:
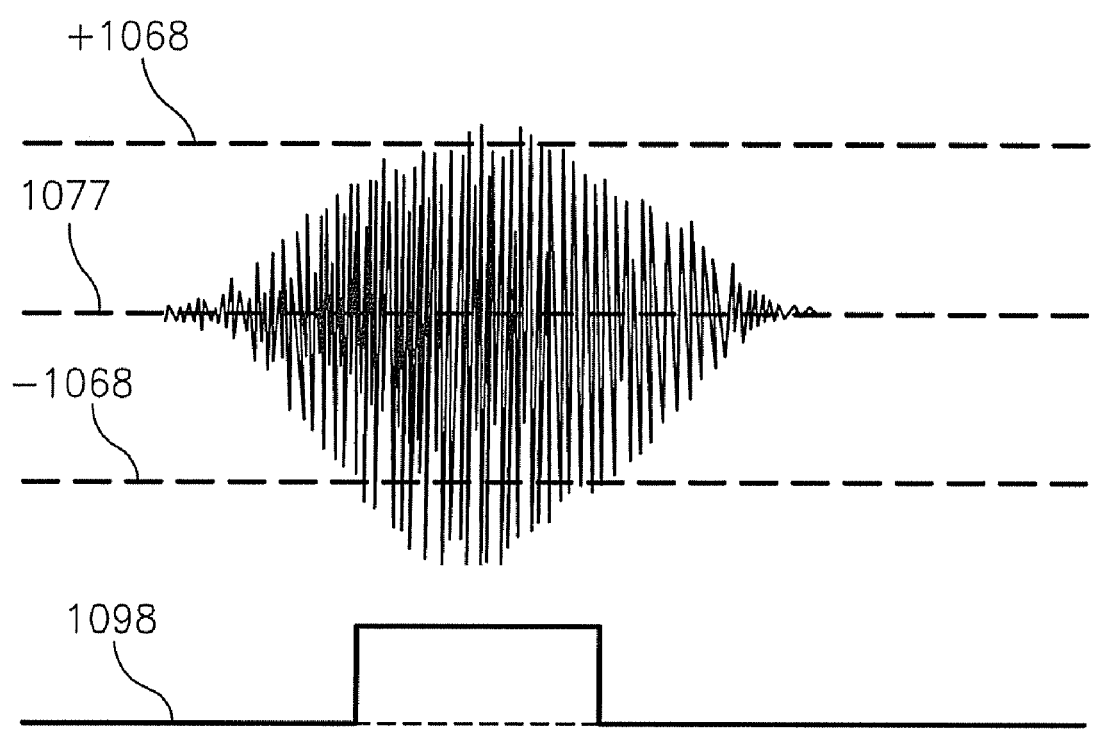
FIG. 12 illustrates an exemplary waveform related to the spoken word "you"

FIG. 12 illustrates an exemplary waveform of the channel 1077 related to the spoken word "you." The waveform is illustrated with respect to the high reference DC level 1068. Peak levels of electrical signals related to the waveform may cause the ADC 81 to enter data overload. The electrical signals are biased towards a negative side of the waveform. The output signal 1098 is also illustrated. The output signal 1098 enters the high state when the channel 1077 crosses the lower threshold (corresponding to the low reference DC level 1069).

Figure 13:
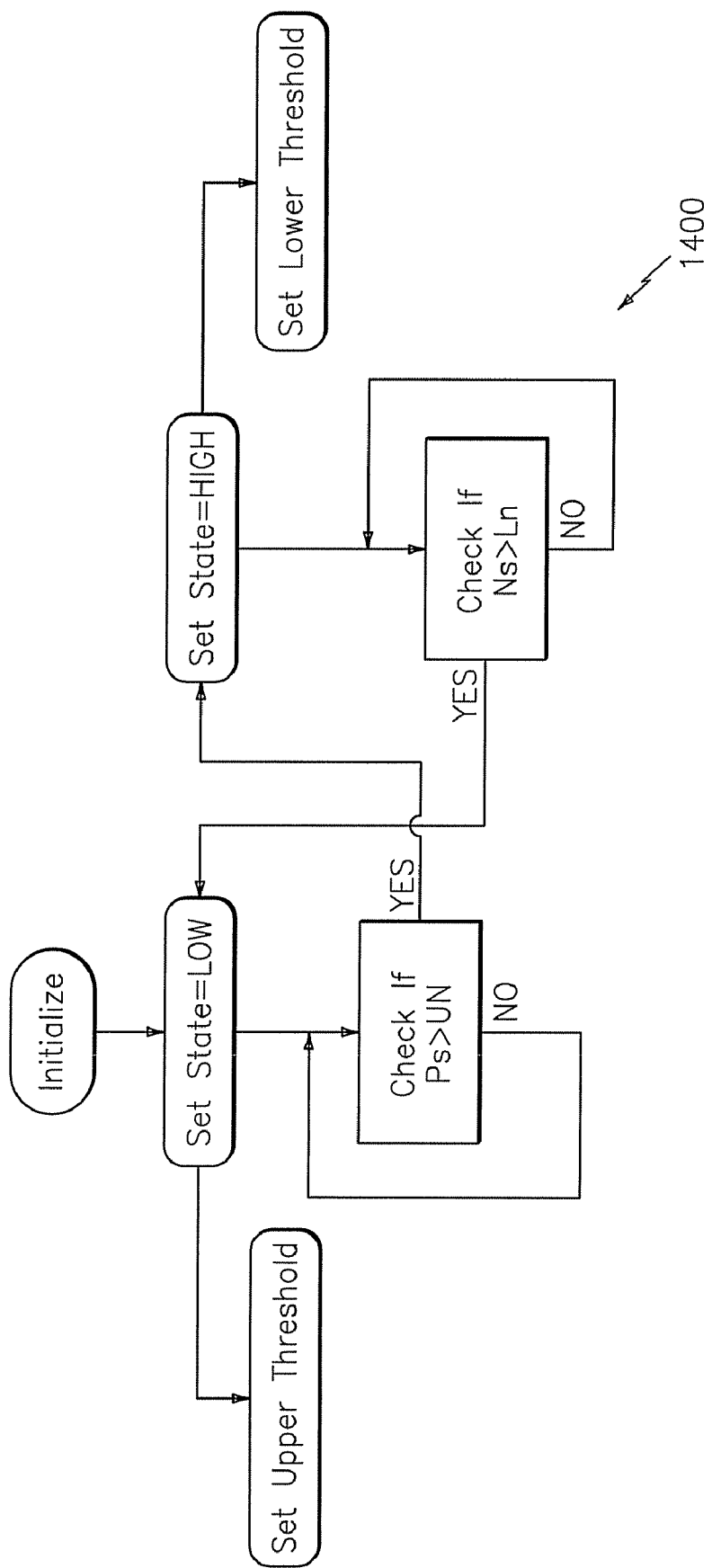
FIG. 13 illustrates an exemplary method for selecting one of a high scaling state and a low scaling state.

FIG. 13 illustrates an exemplary method 1400 for selecting one of a high scaling state and a low scaling state by the MCU 1011 and the scale detector 1050. When the analog base unit 99 is in the low scaling state, the upper threshold is selected by setting the threshold switch 1070 to the high reference DC level 1068. The MCU 1011 samples the output signals 1098 and 1099 (refer to FIG. 11A). A sampling interval is typically 500μ seconds or less to ensure detection of a pulse with duration of 1 millisecond. The MCU 1011 will select the high scaling state when Ps>Un, where Ps is a number of consecutive samples with the high state and Un is 2 to represent a time period of approximately 1 millisecond. Similarly, when the analog base unit 99 is in the high scaling state, the MCU 1011 sets the threshold switch 1070 to the low reference DC level 1069. The MCU 1011 samples the output signals 1098 and 1099. The sampling interval is typically between 500μ seconds and 1 millisecond. The MCU 1011 will select the low scaling state when Ns>Ln, where Ns is a number of consecutive samples with the low state and Ln is 1000 which represents a time period of approximately 0.5 millisecond.

The flow charts depicted herein are just examples. There may be many variations to these charts or the steps (or operations) described therein without departing from the spirit of the invention. For instance, the steps may be performed in a differing order, or steps may be added, deleted or modified. All of these variations are considered part of the claimed invention.

While the invention has been described with reference to an exemplary embodiment, it should be understood by those skilled in the art that various changes may be made and equivalents may be substituted for elements thereof without departing from the scope of the invention. For example, certain ranges, limits, settings, and other such parameters may be modified to further implement the teachings herein. In addition, many modifications may be made to adapt a particular situation or substance to the teachings of the invention without departing from the scope thereof. Therefore, it is important that the invention not be limited to the particular embodiment disclosed as the best mode contemplated for carrying out this invention, but that the invention will include all embodiments falling within the scope of the apportioned claims. Moreover, unless specifically stated any use of the terms first, second, etc. do not denote any order or importance, but rather the terms first, second, etc. are used to distinguish one element from another.

What is claimed is:

1. An interface adapted for use with an audiometer, comprising:
   a digital wireless interface supported by a base unit and a remote unit wherein the base unit receives signals comprising test sound information corresponding to a test sound from the audiometer and provides the signals as digitally encoded test sound information corresponding the test sound to the remote unit via the digital wireless interface.

2. The interface as in claim 1, wherein the digital wireless interface comprises high density coding.

3. The interface as in claim 2, wherein the high density coding comprises minimum shift keying.

4. The interface as in claim 1, further comprising earphones coupled to the remote unit.

5. The interface as in claim 1, further comprising insert earphones coupled to the remote unit.

6. The interface as in claim 1, further comprising a bone conduction transducer coupled to the remote unit.

7. A base unit adapted for receiving signals from an audiometer, comprising:
   a receiver for receiving test sound information corresponding to a test sound and transmitting digitally encoded test sound information corresponding to a test sound to a remote unit through a digital wireless interface.

8. The base unit as in claim 7, further comprising a user interface.

9. The base unit as in claim 7, wherein the base unit comprises at least one of an analog base unit and a digital base unit for receiving the test sound information.

10. The base unit as in claim 7, wherein the base unit comprises a computer-processing unit adapted for running a digital audiometer.

11. A remote unit adapted for providing a test sound, the remote unit comprising:
    a digital wireless interface for receiving digitally encoded test sound information corresponding to a test sound and outputting a test sound signal to a transducer for providing the test sound.

12. The remote unit as in claim 11, further comprising a response switch configured to communicate actuation of the response switch to a base unit via the digital wireless interface.

13. A method for conducting an audiometric test of a test subject, the method comprising:
    receiving test sound information from an audiometer;
    digitally encoding the test sound information into digitally encoded test sound information corresponding to a test sound;
    transmitting the digitally encoded test sound information corresponding to the test sound using a digital wireless interface;
    converting the digitally encoded test sound information into the test sound information; and
    providing the test sound information to the test subject as at least one test sound.

14. The method as in claim 13, further comprising calibrating a sound pressure level of the at least one test sound to at least one ear canal of the test subject.

15. The method as in claim 13, further comprising identifying an ear canal of the test subject to which a masking sound is transmitted.

16. The method as in claim 13, further comprising transmitting a masking sound to an ear canal of the test subject.

17. The method as in claim 13, further comprising measuring ambient noise in at least one ear canal of the test subject.

18. The method as in claim 13, further comprising canceling ambient noise in at least one ear canal of the test subject.

19. The method as in claim 13, further comprising sending a response via a response switch from the test subject.

20. A system for conducting an audiometric test, the system comprising:
    means for receiving test sound information for the audiometric test;
    means for producing digitally encoded test sound information corresponding to a test sound from the test sound information;
    means for transmitting the digitally encoded test sound information corresponding to the test sound over a digital wireless interface;
    means for receiving the digitally encoded test sound information; and
    means for producing test sounds from the digitally encoded test sound information.

21. The system as in claim 20, further comprising means for calibrating a sound pressure level of at least one test sound to at least one ear canal of a test subject.

22. The system as in claim 20, further comprising means for transmitting a masking sound to an ear canal of a test subject.

23. The system as in claim 20, further comprising means for identifying an ear canal of a test subject to which a masking sound is transmitted.

24. The system as in claim 20, further comprising means for measuring ambient noise in at least one ear canal of a test subject.

25. The system as in claim 20, further comprising means for canceling ambient noise in at least one ear canal of a test subject.

26. The system as in claim 20, further comprising means for sending a response from a test subject.

27. The system as in claim 20, further comprising means for generating test sound information.

28. An audiometer adapted for providing input to a remote unit, comprising:
- a test sound information generator for generating test sounds and a transceiver for transmitting the test sounds as digitally encoded test sound information corresponding to the test sounds to the remote unit through a digital wireless interface.

29. A method for calibrating an audiometric testing system having a digital wireless interface, the method comprising:
- producing a test sound in an ear canal of a test subject, the producing using the digital wireless interface to transmit the test sound as digitally encoded test sound information corresponding to the test sound;
- monitoring a corresponding sound pressure level; and
- adjusting the audiometric testing system via the digital wireless interface to match the sound pressure level to a predetermined value.

30. An interface for providing an appropriate dynamic range for audiometric testing comprising:
- a digital wireless interface supported by a base unit and a remote unit wherein the base unit receives a signal comprising test sound information corresponding a test sound from an audiometer and provides the signal as digitally encoded test sound information corresponding to the test sound to the remote unit via the digital wireless interface, wherein the amplitude of the signal provided via the wireless interface is automatically scaled based on a comparison of an average amplitude of the signal to preset thresholds.

* * * * *

UNITED STATES PATENT AND TRADEMARK OFFICE
CERTIFICATE OF CORRECTION

PATENT NO. : 8,196,470 B2
APPLICATION NO. : 11/679959
DATED : June 12, 2012
INVENTOR(S) : Allan H Gross It is certified that error appears in the above-identified patent and that said Letters Patent is hereby corrected as shown below:

Column 11
Line 24, delete "resealing" and insert -- rescaling -- therefor.

Column 12
Lines 30-61, delete "During the .........being used," and insert the same on Col. 12, Line 29, after "masking" as a continuation of the paragraph.

Column 13
Line 28, delete "band" and insert -- bank -- therefor.

Column 14
Line 9, delete "farther" and insert -- further -- therefor.

Signed and Sealed this
Twenty-fifth Day of December, 2012

David J. Kappos
*Director of the United States Patent and Trademark Office*